US008530426B2

(12) United States Patent
Lintner et al.

(10) Patent No.: US 8,530,426 B2
(45) Date of Patent: Sep. 10, 2013

(54) COSMETIC OR DERMOPHARMACEUTICAL COMPOSITION COMPRISING AT LEAST ONE UDP GLUCURONOSYL TRANSFERASE (UGT) ENZYMES INDUCER

(75) Inventors: Karl Lintner, Rambouillet (FR); Claire Mas Chamberlin, Chevreuse (FR)

(73) Assignee: Sederma SAS (FR)

( * ) Notice: Subject to any disclaimer, the term of this patent is extended or adjusted under 35 U.S.C. 154(b) by 973 days.

(21) Appl. No.: 11/587,533

(22) PCT Filed: Apr. 25, 2005

(86) PCT No.: PCT/IB2005/051344
§ 371 (c)(1),
(2), (4) Date: Sep. 19, 2007

(87) PCT Pub. No.: WO2005/102266
PCT Pub. Date: Nov. 3, 2005

(65) Prior Publication Data
US 2008/0213198 A1  Sep. 4, 2008

(30) Foreign Application Priority Data

Apr. 26, 2004  (FR) ..................................... 04 04408

(51) Int. Cl.
*A61P 17/00* (2006.01)

(52) U.S. Cl.
USPC ........... 514/18.8; 514/844; 514/1.1; 514/425; 424/401

(58) Field of Classification Search
USPC .................. 424/401; 514/1.1, 18.8, 425, 844
See application file for complete search history.

(56) References Cited

U.S. PATENT DOCUMENTS

| | | | |
|---|---|---|---|
| 5,821,237 A * | 10/1998 | Bissett et al. ................... 514/75 |
| 5,952,373 A * | 9/1999 | Lanzendorfer et al. ....... 514/456 |
| 2002/0160965 A1* | 10/2002 | Lanzendorfer et al. ......... 514/27 |
| 2003/0147830 A1* | 8/2003 | Phillips et al. ............. 424/70.14 |
| 2003/0161832 A1* | 8/2003 | Bander ...................... 424/155.1 |
| 2004/0115766 A1 | 6/2004 | Lintner |
| 2004/0120918 A1 | 6/2004 | Lintner et al. |
| 2005/0142092 A1 | 6/2005 | Lintner |
| 2006/0067905 A1 | 3/2006 | Lintner et al. |
| 2006/0110343 A1 | 5/2006 | Lintner |
| 2006/0165643 A1 | 7/2006 | Lintner |
| 2006/0239957 A1 | 10/2006 | Lintner |
| 2007/0043109 A1 | 2/2007 | Linter et al. |
| 2009/0010976 A1 | 1/2009 | Lintner |
| 2009/0017147 A1 | 1/2009 | Lintner et al. |
| 2009/0029926 A1 | 1/2009 | Lintner |
| 2009/0186826 A1 | 7/2009 | Lintner et al. |
| 2009/0214607 A1 | 8/2009 | Lintner et al. |
| 2009/0253666 A1 | 10/2009 | Lintner et al. |
| 2009/0269395 A1 | 10/2009 | Lintner et al. |
| 2010/0285077 A1 | 11/2010 | Lintner et al. |
| 2011/0002865 A1 | 1/2011 | Fournial et al. |
| 2011/0033507 A1 | 2/2011 | Lintner et al. |
| 2011/0045036 A1 | 2/2011 | Lintner et al. |

FOREIGN PATENT DOCUMENTS

| | | |
|---|---|---|
| DE | 100 09 424 A1 | 9/2001 |
| DE | 10050155 A1 * | 4/2002 |
| EP | 1 300 138 A2 | 4/2003 |
| FR | 2 594 336 A1 | 8/1987 |
| FR | 2 778 663 A1 | 11/1999 |
| FR | 2 802 413 A1 | 6/2001 |
| FR | 2 836 042 A1 | 8/2003 |
| WO | WO-00/67767 A1 | 11/2000 |
| WO | WO-02/076423 A2 * | 10/2002 |
| WO | WO-2004/089392 A1 | 10/2004 |

OTHER PUBLICATIONS

Database Embase 'Online! Elsevier Science Publishers, Amsterdam, NL, 2002, Walle U K et al., Induction of human UDP-glucuronsyltransferase UGT1A1 by flavonoids—Structural requirements XP002309670 Database accession No. EMB-2002159263 abstract & Drug Metabolism and Disposition 2002 US, vol. 30, No. 5, 2002, pp. 564-569 ISSN: 0090-9556.

Patent Abstract of Japan, vol. 2000, No. 14, Mar. 5, 2001 & JP 2000 319154 A (Nippon Menaade Keshohim KK: Ichimura Pharcos Co. Ltd.), Nov. 21, 2000.

Database WPI Derwent Publications Ltd., London, GB; AN 2001-481491 XP002309671 Cheoung J H et al.: Chrysin 7-o-crotonate, its producing method and composition useful for hair growth tonic & KR 2001 009 474 A (Cheoung J H, Kim P K) Feb. 5, 2001.

Anonymous: "Nutrasport Testroxin Gel" Internet Article, 'Online! pp. 1-2, XP02309667 Global-Nutrition-inc. Retrieved from the Internet: ULR:http://www/bodybuilding-supplements-for-you.com/nutrasport/testroxin-gel.htm> Nov. 29, 2002.

International Antiaging Systems: "Estrogen Blockers" Internet Article, 'Online! pp. 1-2 XP002309668 Retrieved from the Internet: ULR:http://www.antiaging-systems.com.a2z.estrogenblock.htm, Apr. 4, 2001.

Ahn et al., Antioxidant Activity and Constituents of Propolis Collected in Various Areas of Korea, Journal of Agriculture and Food Chemistry, vol. 52, pp. 7286-7292 XP002309669 Feb. 11, 2004 American Chemical Society.

Database Embase 'Online! Elsevier Science Publishers, Amsterdam, NL, 2002, Walle UK et al., Induction of human UDP-glucuronsyltransferase UGT1A1 by flavonoids—Structural requirements XP002309670 Database accession No. EMB-2002159263 abstract & Drug Metabolism and Disposition 2002 US, vol. 30, No. 5, 2002, pp. 564-569 ISSN: 0090-9556.

\* cited by examiner

*Primary Examiner* — Ali Soroush
(74) *Attorney, Agent, or Firm* — Lerner, David, Littenberg, Krumholz & Mentlik, LLP

(57) ABSTRACT

The invention relates to topical use of at least one UGT inducer for the preparation of a cosmetic or dermopharmaceutical composition comprising a dermatologically acceptable carrier to protect and/or enhance the state of the skin and prevent and/or treat imperfections of the skin.

26 Claims, No Drawings

COSMETIC OR DERMOPHARMACEUTICAL COMPOSITION COMPRISING AT LEAST ONE UDP GLUCURONOSYL TRANSFERASE (UGT) ENZYMES INDUCER

SUMMARY OF THE INVENTION

The invention concerns a new cosmetic or dermopharmaceutical composition to protect and/or enhance the state of the skin and prevent and/or treat imperfections of the skin.

BACKGROUND OF THE INVENTION

Cosmetic products that temporarily improve the appearance of the skin by masking the irregularities with an opaque cosmetic film are available. This invention proposes an effective alternative to the use of those masking cosmetic products to prevent and/or treat skin that has aged and/or is subject to environmental aggression.

Throughout life, each individual is subject to exposure to sunlight and air pollution either occasionally or to multiple and/or extreme exposures. The skin continuously suffers aggression from numerous extrinsic but also intrinsic factors. The extrinsic factors include ultraviolet radiation (mainly linked to exposure to the sun: sunlight-induced aging), environmental pollution and atmospheric pollution, but also wind, heat, low relative humidity levels, contact with household surfactants and other chemicals, abrasives, smoking, alcohol, drugs, diet, stress, mechanical stress, severe atmospheric conditions and so on. The intrinsic factors include chronological aging and the other biochemical changes in the skin. The following may also be cited: hormonal upheavals, fatigue, acne, obesity, tanning, diets, disease, for example, hyperbilirubinemia (jaundice), hematomas and disorders of the blood microcirculation.

Whether extrinsic or intrinsic, those factors induce cosmetically undesirable impairment of the visible appearance, clinical and physical properties and physiological and histological functions of the skin and even give rise to visible signs of (premature or non-premature) aging of the skin.

The most noteworthy and patent changes include dryness and the development of fine lines and wrinkles, loss of elasticity, wasting and sagging of the skin, loss of firmness, thinning of the skin, loss of uniformity of the complexion, a dull complexion, hyperpigmentation, senile lentigines, red spots, a rough, coarse surface texture and a marbled pigmentation. Dull and impaired hair, hair loss and an unbalanced scalp are also frequent symptoms.

Other less obvious but nonetheless measurable changes occur when the skin ages or is subject to chronic environmental aggression and include a general reduction in the vitality of the tissues and cells, slowed cell replication, a decrease in protein synthesis, an increase in proteolysis, a decrease in cutaneous blood circulation or vasodilatation with blood stasis, seepage from the blood compartment, reduced water content, an accumulation of errors in the structure and function of proteins, a deleterious change in the skin's barrier properties, connective tissues and cohesion, and a reduced ability of the skin to remodel and repair itself.

In particular, in the case of secondary effects related to accumulation of iron in the peripheral cutaneous tissues, such as hyperbilirubinemia (jaundice, neonatal icterus), hematoma, and rings (or circles) under the eyes, pigmentation is promoted by the inadequate elimination of hemolysis products: violet-green appearance of biliverdin, brown-red-or-ange with bilirubin and mineral iron, violet with hemosiderin.

For many people, an impaired or aged skin reminds them of the disappearance of youth. For that reason, our societies attribute great importance to apparent youth and fighting against deteriorated/damaged/imperfect skin has become an economic issue. The treatments proposed range from functional cosmetic creams to cosmetic surgery.

External factors, like internal factors, supply the body with a great variety of substances that are both exogenous (xenobiotics) and endogenous. Those substances, frequently lipophilic, have a high affinity for the skin that is itself lipid-based. The skin surface concentrates all the substances that impair the skin and contribute to its imperfection.

BRIEF SUMMARY OF THE INVENTION

We have now discovered that the essential characteristics of deteriorated/imperfect skin are frequently the presence of xenobiotics and/or the abnormal accumulation of endogenous substances. In consequence, the use of at least one UGT-inducer could enable a preventive and/or curative effect on deteriorated/imperfect skin to be obtained.

We have also demonstrated the presence of UGT enzymes in the human skin. Stimulation of those cutaneous enzymes has never been tested and the topical use of an UGT-inducer to protect the skin and/or enhance its state has never been proposed. The applicant has discovered that topical application of a UGT-inducer stimulates the expression of those enzymes.

Many compounds have been described as being useful for improving skin appearance and physiology, including reducing fine lines, wrinkles and other symptoms associated with aged or photodamaged skin. Many compositions are available on the world wide market. But improvement is always desirable.

Surprisingly, we have discovered that the use of at least one UDP-GT (still known as UGT) inducer, applied topically, has a beneficial effect on the improvement in the general condition of the skin that is not already known to the state of the art to the inventors' knowledge.

In particular, topical application of UGT-inducers may reduce (preventively and/or curatively) the visible and/or tactile discontinuities of the skin, including fine lines, wrinkles, enlarged pores, roughness, dryness, the loss of uniformity of the complexion, hematoma, rings under the eyes and other deteriorated textures and/or appearances of the skin, in other words reduce or efface the deterioration of the skin associated with aged, photo-damaged skin subject to environmental aggression. UGT-inducer application can also prevent and/or reduce and/or efface the aggressions and/or imperfections and/or deteriorations such as hematomas and rings under the eyes.

Bilirubin is normally eliminated via conjugation with glucuronic acid thanks to a series of enzymes: the UDP glucuronosyl transferases, more usually known as UGT. When the UGTs are not very effective, bilirubin accumulates and the skin changes color. This is the case in neonatal jaundice, hematomas and rings under the eyes.

It has now been found that topical application of an UGT-inducer may reduce the coloration induced by these blood pigments.

The previous state of the art did not supply all the advantages and benefits of the present invention.

For that reason, the present invention relates to the topical use of at least one UGT-inducer in or for the preparation of a cosmetic or dermopharmaceutical composition containing an acceptable dermatological carrier to protect and/or enhance the state of the skin and prevent and/or treat imperfections of the skin. One aspect of the present invention relates to cosmetic or dermopharmaceutical compositions including at least one UGT enzymes inducer and an acceptable dermatological carrier to protect and/or enhance the state of the skin and prevent and/or treat imperfections of the skin.

Another aspect of the present invention also relates to cosmetic or dermopharmaceutical compositions including at least one UGT enzymes inducer and an acceptable dermatological carrier to stimulate the process of detoxification, and purification of the body and metabolism of xenobiotics.

Another aspect of the present invention relates to cosmetic or dermopharmaceutical compositions including at least one UGT enzymes inducer and an acceptable dermatological carrier to increase the detoxification of xenobiotics, modulate the conversion of androgens and estrogens, increase muscle mass, intervene at pigmentation level, inhibit melanogenesis, protect the body against pollution, stimulate the detoxification systems, stimulate hair and body hair growth, modulate DHT levels, intervene on adipocytes and promote lipolysis Another aspect of the present invention also relates to cosmetic or dermopharmaceutical compositions including at least one UGT enzymes inducer and an acceptable dermatological carrier to prevent and/or to treat and/or to reduce the disorders of the blood microcirculation such as hyperbilirubinemia (jaundice), hematoma and rings under the eyes.

The UGT-inducer according to the invention stimulates one or several isoforms of the UGT enzyme family. The inducer may be a flavonoid compound or one of its stereoisomers or a derivative of a flavonoid compound, an analog of a flavonoid compound or a glycoside of a flavonoid compound. Those compounds may be extracted from natural material or occurred by chemical synthesis.

Another aspect of the present invention also relates to an original combination of UGT-inducers and at least one of a carrier, a cosmetic ingredient commonly used in the cosmetic industry, active substances or principal adjuvant.

Preferred embodiments include both a UGT-inducer and at least one peptide derivative. A composition fully illustrating the present invention combines a UGT-inducer (chrysin-), an iron-chelating agent (N-hydroxysuccinimide) and peptides (e.g. N-Palmitoyl-Gly-Gln-Pro-Arg (SEQ ID NO:1) and N-Palmitoyl-Gly-His-Lys) to treat circles under the eyes.

Certain aspects of the present invention also relate to the use of such compositions to make cosmetics, personal care products, topical dermopharmaceutical ou vetenary preparation or a drug to protect and/or improve the state of the skin and/or the hairs, and/or mucosa, and to prevent and/or treat imperfections of the skin. This is accomplished by topical application of said medicament to the skin of the human or the mammal needing such treatment.

Certain aspects of the present invention also relate to methods of protecting, improving the state of the skin, preventing and/or treating imperfections of the skin of a person in need thereof comprising the steps of providing at least one UGT inducer and a carrier or a cosmetic or dermopharmaceutical composition comprising at least one UGT inducer. These methods generally consisting in topically applying the composition to the skin, to the hairs and/or to the mucosa when needed, in the amount and at the frequency best suited for the purpose. Methods of preventing, delaying the onset, or treating a skin condition are also contemplated.

DETAILED DESCRIPTION

We have observed that a pathophysiological situation common to all states of aggressed and/or deteriorated and/or imperfect skin is linked to the presence in the tissues of endogenous and/or exogenous substances and/or to slowed and/or inadequate UGT enzyme function.

In order to stimulate the processes of detoxification, purification of the body and metabolism of xenobiotics, the present invention thus proposes the topical use of at least one UGT-enzyme inducer.

The UGT or UGTs or UDP-GTs or uridine diphosphoglucuronosyl transferase or UDP-glucuronosyl transferase (herein referred to as UGT) constitute a superfamily of enzymes mainly present in the liver.

These enzymes are key detoxification enzymes (known as phase II enzymes) for a large number of exogenous compounds. The enzymes bind the compound, which is generally lipophilic, with glucuronic acid, thus rendering it hydrophilic, transportable and excretable by the urinary route. This process is known as "glucuroconjugation". Those enzymes catalyze the glucuronidation of xenobiotics such as carcinogens by, in general, rendering them biologically inactive.

UGT also play an important role in the metabolism of endogenous compounds. This type of coupling is widely used by the body to eliminate numerous endogenous substances such as steroids (β-estradiol, testosterone), thyroid hormone, retinoic acid and, in particular, bilirubin derived from the blood hemoglobin recycling cycle at the end of the erythrocytes' lifespan.

In certain cases, glucuroconjugation may transform a substrate into a glucuronide substrate that is more active or active on other receptors. The amplification of the beneficial effects of a substrate by activating its glucuroconjugation may thus be envisaged.

Important for the body, those enzymes are able to adjust their level of activity as a function of the task incumbent on them: they are inducible.

Some 15 isoforms have been identified to date and divided into 2 series: UGT1A and UGT2B.

With regard to induction of the expression of UDP-glucuronosyl transferase, various isoforms may be induced separately or concomitantly, depending on the inducing agent. In the following, the terms UGT or UDP-glucuronosyl transferase may designate one or the other of the isoforms of UGT, both, or even all the isoforms.

In one preferred aspect of the invention, the UGT-inducing agent is a substance that stimulates one or several isoforms of the UGT enzyme family.

The terms "UGT-inducing agent", "UGT enzyme inducing agent" or "UGT inducer", as used herein, mean any substance, simple or complex compound, of natural or synthetic origin, able to induce, stimulate or increase the activity of the UGT enzymes and/or able to induce, increase or accelerate the reaction catalyzed by that enzyme.

We have discovered the beneficial effect of increasing the level of UGT expression by topical use of at least one UGT enzyme inducing agent in order to (without this list being restrictive): increase the detoxification of xenobiotics (e.g. carcinogens), modulate the conversion of androgens and estrogens (modulate the steroid levels in the skin via UGT, anti-aging effect), increase muscle mass, intervene at pigmentation level, inhibit melanogenesis, protect the body against pollution, stimulate the detoxification systems, stimulate hair and body hair growth, modulate DHT levels, intervene on adipocytes and promote lipolysis.

UGT inducer are used in cosmetic or dermopharmaceutical compositions as per the invention at concentrations which may be range from about 0.000001% to about 10% (w/w), preferably from about 0.00001% to about 1% (w/w), and most preferably from about 0.0001% to about 0.1% (w/w), by weight of the composition.

According to the invention, the UGT enzyme inducer may be a flavonoid compound or one of its stereoisomers, a derivative of a flavonoid compound, an analog of a flavonoid compound or a glycoside of a flavonoid compound. These may be collectively referred to as "flavonoid compounds" as the context will allow.

The UGT-inducing agent may thus be a member of the flavonoid family, including the flavanones, flavones, isoflavones, flavonols, dihydroflavonols, catechins, leukoanthocyanidins, coumarins and isocoumarins, chalcones, etc. These flavonoid compounds may be in hydroxylated or methoxylated form, in the form of one of their stereoisomers, or in the form of natural (glucoside, galactoside, fructoside, rhamnoside, rutinoside, arabinoside, xyloside, apioglucosiderobinoside), or non-natural glycoside derivatives.

Under the terms of the invention, the UGT enzyme-inducing agent may have (without this list being restrictive) the chemical structure of a derivative or analog of the following molecules: chrysin, techtochrysin, chrysin 5-methylether, galangin, galangin 5-methylether, pinocembrin, pinobanksin, apigenin, fisetin, hesperitin, kaempferol, morin, myrecetin, naringenin, quercetin, quercitin, rutin, myricetin, rhamnetin, luteolin, naringin, hesperidin, naringenin, hesperitin, phloridzin, diosmin, fisetin, vitexin, neohesperidin dihydrochalcone, glucosyl rutin, genistein, alpha-glucosylrutin, alpha-glucosylmyrictrin, alpha-glucosylisoquercitrinitrin, alpha-glucosylquercitrin, troxerutin, monoxerutin, phlorizin, robinetin, gossypetin, taxifolin, eriodictyol, troxerutin, tangeretin, catechin, epicatechin, gallocatechin, epigallocatechin, epigallocatechin gallate, epicatechin gallate, toringin, primetin, cosmosiin, apiin, galuteolin, glucoluteolin, acacetin, linarin, diosmetin, baicalein, trifolin, astragalin, roninin, kaempferitrin, isoquercitrin-datiscetin, quercetagetin, quercetagitrin, rhamnetin, isorhamnetin, wogonin, scutellarein, cyanidin, delphinidin, pelargonidin, calycopterin, isovitexin, alpha-gisoquercitrintin, alpha-mannosylrutin, nepetin, tangeretin, tricetin, tricin, pinocembrin, biochanin A, daidzein, puerarin, umbelliferone, esculin, esculoside, esculetin scopoletin, berberin, dimers: amentoflavone, ginkgetin, isoginkgetin, pharmaceutical derivatives: androstanediol, bilirubin, codeine, ethynylestradiol, furosemide, gemfibrozil, hydromorphone, hyodeoxycholic acid, imipramine, ketoprofen, morphine, naloxone, 1-naphthol, naproxene, propofol, valproic acid and derivatives, zidovudine, lamotrigine and gamma-orizanol.

The flavonoid compounds, theirs stereoisomers, derivatives, analogs or glycosides of a flavonoid compound may be found in any source of supply, in particular by chemical synthesis, enzymatic synthesis, by one of many biotechnology processes or by plant extraction. These compounds can be extracted from plant such as *Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae* and *Zingiberacea, Achyrocline Actinodaphne, Acacia, Alpinia, Alnus sieboldiana, Anaphalis, Artocarpus, Baccharis, Buchenavia, Centaurea, Colebrookea, Cotula, Cyclanthera pedata* (achoccha), *Derris, Desmos, Docyniopsis tschonoski, Dolichandrone falcata, Enkianthus* sp, *Eupatorium, Ficus, Flourensia, Glycyrrhiza, Gnaphalium, Helichrysum, Lindera, Malus* spp, Molsa, *Millettia, Notholaena, Origanum, Oroxylum, Pityrogramma, Pinus, Pongamia, Prunus, Sapium, Sarothamnus patens, Scutellaria, Spartium junceum, Stachys, Tephrosia, Ulmus, Ziziphora.* This compounds can be obtained as extracts from natural sources such as extracts of sheets of tea (*Camellia sinensis* or *Camellia japonica*) in particular green tea extracts, extracts of St. John's wort (Hypericum perforatum), *Echinacea* extract, ginseng extract, garlic extract, gingko extract, extract of *Glycyrrhiza Glabra* root (licorice), extract of Brussels sprouts (*Brassica oleracea*), extract of passionflower (*Passiflora incarnata*), Yin Chin extract, eugenol, *glycyrrhizin*, glaucin, the organosulfide compounds of *Ailiacea*.

Preferred UGT enzyme-inducer may be, in particular, certain flavonoids and, most preferred chrysin or one of its stereoisomers or a derivative, analog or glycoside thereof.

Chrysin (5,7-dihydroxyflavone) is a fairly common flavonoid in the plant kingdom. Its antioxidant properties and anti-inflammatory activity have been widely reported in the literature.

The present invention concerns the topical use of chrysin, its analogs, its stereoisomers, its glycosides and their derivatives as detoxification-inducing agents. These may be collectively referred to as "chrysin" as the context will allow. In particular, chrysin is used as an agent against rings under the eyes. Chrysin may be used to eliminate the hemoglobin degradation products which result in the formation of bilirubin (orange-colored pigment) which accumulates in the skin.

UGT-inducing agents and, in particular, flavonoids, and more particularly, chrysin, their analogs and derivatives, may thus eliminate heme degradation products and hence bilirubin and iron from the rings under the eyes and hematoma.

Under the terms of the invention, chrysin analogs and compositions containing them may be used. A chrysin analog with a flavonoid structure may be envisaged. Similarly, a chrysin analog with a flavone structure may be envisaged. A chrysin analog with a 5,7-substituted flavone structure is particularly envisaged (including, but not restricted to: quercetin, apigenin, luteolin and diosmetin).

Chrysin or 5,7-dihydroxyflavone, is present naturally in many trees and plants such as *Pinus aristata, Prunus domestica, Pelargonium* species, *Pinaceae* species including *Pinus, Passiflora* species (*Passiflora coerulea L., Passiflora incarnata*) including tropical Passion fruit, propolis, *Daucus carota, Eriodictyon californicum, Eucalyptus globulus, Populus nigra, Populus tacamahacca, Prunus cerasus, Scutellaria baicalensis, Scutellaria galericulata, Spartium junceum, Ulmus sieboldiana, Flourensia resinosa, Oroxylum indicum.*

In one embodiment the composition of the present invention contains a plant extract, preferably a passion flower extract as a supply of UGT inducer. The quantity of plant extract, such as passion flower extract, to be incorporated in the cosmetic or dermopharmaceutical composition lies between 0,01 and 100% (w/w), preferentially between 0,1 and 10% in weight of the final total composition.

In one embodiment the composition comprises at least one UGT inducer, a carrier, and at least one of active substances intended to prevent and/or imperfections of the skin.

The term "dermatologically acceptable," as used herein, means that the compositions or components described are suitable for use in contact with human or mammalian skin without risk of toxicity, incompatibility, instability, allergic response, and the like. 'Dermatologically acceptable carrier' is taken to mean, under the terms of the present invention (without being restrictive): an aqueous or dilute alcoholic solution, a water-in-oil emulsion, an oil-in-water emulsion, a microemulsion, an aqueous gel, an anhydrous gel, a serum or a vesicle dispersion.

All terms such as "skin aging," "signs of skin aging," "topical application," and the like are used in the sense in which they are generally and widely used in the art of developing, testing and marketing cosmetic and personal care products. The term "cosmetic composition" or more briefly just "composition" in accordance with the present invention relates to a formulation that can be used for cosmetic purposes, purposes of hygiene or as a basis for delivery of one or more pharmaceutical ingredients. It is also possible that these formulations are used for two or more of these same purposes at one time. A medicated dandruff shampoo, for example, has pharmacological properties and is used as a personal care product to provide clean hair.

At a minimum, these compositions include one UGT inducer. These compositions can also include additional ingredients as a carrier dermatologicaly acceptable.

"Cosmetics," as used herein, include without limitation, lipstick, mascara, rouge, foundation, blush, eyeliner, lipliner, lip gloss, facial or body powder, sunscreens and blocks, nail polish, mousse, sprays, styling gels, nail conditioner, whether in the form of creams, lotions, gels, ointments, emulsions, colloids, solutions, suspensions, compacts, solids, pencils, spray-on formulations, brush-on formulations and the like.

Personal care products include, without limitation, bath and shower gels, shampoos, conditioners, cream rinses, hair dyes and coloring products, leave-on conditioners, sunscreens and sunblocks, lip balms, skin conditioners, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, deodorants, cleansers, skin gels, rinses, whether in solid, powder, liquid, cream, gel, ointment, lotion, emulsions, colloids, solutions, suspensions, or other form.

Pharmaceutical preparations in accordance with the present invention include, without limitation, carriers for dermatological purposes, including topical and transdermal application of pharmaceutically active ingredients. These can be in the form of gels, patches, creams, nose sprays, ointments, lotions, emulsions, colloids, solutions, suspensions, powders and the like.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye rings), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

As used herein, prophylactically regulating a skin condition includes delaying, minimizing and/or preventing visible and/or tactile discontinuities in skin (e.g., texture irregularities in the skin which may be detected visually or by feel), including signs of skin aging.

As used herein, therapeutically regulating skin condition includes ameliorating, e.g., diminishing, minimizing and/or effacing, discontinuities in skin, including signs of skin aging. Some of the products produced using the compositions of the present invention and indeed the compositions themselves may be used for prophylactically or therapeutically regulating a skin condition.

Some of the products and compositions of the present invention are useful for improving skin appearance and/or feel. For example, preferred compositions of the present invention are useful for improving the state of the skin that is imperfect or subject to aggression by providing an immediate visual improvement in skin appearance following application of the composition to the skin. Generally speaking, compositions of the present invention which further contain particulate materials will be most useful for providing the immediate visual improvement.

Some of the compositions of the present invention may also provide additional benefits, including stability, absence of significant (consumer-unacceptable) skin irritation, anti-inflammatory activity and good aesthetics.

While the specification concludes with the claims particularly pointing and distinctly claiming the invention, it is believed that the present invention will be better understood from the following description. The terms "having" and "including" are to be construed as openended unless the context suggests otherwise.

All percentages and ratios used herein are by weight of the total composition and all measurements made are at 25° C. unless otherwise designated.

The compositions of the present invention can comprise (open ended) or consist essentially of the components of the present invention as well as other ingredients described herein. As used herein, "consisting essentially of" means that the composition or component may include additional ingredients, but only if the additional ingredients do not materially alter the basic and novel characteristics of the claimed compositions or methods. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained.

The compositions of the present invention generally contain at least one additional ingredient. The compositions of the present invention may contain a plurality of additional ingredients as well.

In a preferred embodiment, where the composition is to be in contact with human or mammalian keratinous tissue, the additional ingredients should be suitable for application to keratinous tissue, that is, when incorporated into the composition they are suitable for use in contact with human keratinous tissue (hair, nails, skin, lips) without undue toxicity, incompatibility, instability, allergic response, and the like within the scope of sound medical judgment. The CTFA Cosmetic Ingredient Handbook, Ninth Edition (2002) describes a wide variety of nonlimiting cosmetic and pharmaceutical ingredients, commonly used in the skin care industry, which are suitable for use as additional ingredients in the compositions of the present invention. Non-limiting examples of these additional ingredient classes include: healing agents, anti-aging agents, anti-wrinkle agents, moisturizers, antibacterial agents, pesticides, antifongic agents, anti-inflammatory drugs, anti-pruriginous agents, anaesthetic, antiviral agents, keratolytic agents, free radicals scavengers, antiseborrheic, antidandruff agents, anti-acne agents, the agents modulating the differentiation, proliferation or pigmentation of the skin and agents accelerating penetration, cleaning agents, hair conditioning agents, skin conditioning agents, hair styling agents, antidandruff agents, hair growth promoters, Fragrances, sunscreen and/or sunblock compounds, pigments, film formers, hair colors, make-up agents, detergents, pharmaceutical drugs, thickening agents, emulsifiers, humectants, emollients, antiseptic agents, deodorant actives, dermatologically acceptable carriers, surfactants, abrasives, absorbents, aesthetic components such as fragrances, colorings/colorants, essential oils, skin sensates, astringents, etc. (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), antioxidants, binders, biological additives, enzymes, enzymatic inhibitors, enzyme-inducing agents, coenzymes, plant extracts, ceramides, peptides, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), quaternary derivatives, agents increasing the substantivity, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents and derivatives (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof, and lignans.

Such additional ingredients can be selected from the group consisting of the composition of any of claims - - -, wherein said optional ingredient is selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, bisabolol, salicylic acid compounds, peptides and their derivatives, di-, tri-, tetra-, penta-, and hexapeptides and their derivatives, lys-thr-thr-lys-ser (SEQ ID NO:2), palmitoyl-lys-thr-thr-lys-ser (SEQ ID NO:3), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins and their salts and derivatives, provitamins and their salts and derivatives, water soluble vitamins, vitamin B, vitamin B derivatives, vitamin B1, vitamin B2, vitamin B6, vitamin B12, vitamin K, vitamin K derivatives, pantothenic acid, pantothenyl ethyl ether, panthenol, biotin, amino acids and their salts and derivatives, N-acyl amino acid compounds, water soluble amino acids, asparagine, alanine, indole, glutamic acid, water insoluble vitamins, vitamin A, vitamin D, vitamin E, vitamin F, water insoluble amino acids, tyrosine, tryptamine, particulate materials, sunscreen actives, anti-cellulite agents, anti-acne agents, keratolytic agents, butylated hydroxytoluene, butylated hydroxyanisole, allantoin, tocopherol nicotinate, tocopherol, tocopherol esters, palmitoyl-gly-his-lys, phytosterol, dexpanthenol, panthenol, anti-wrinkle agents, anti-atrophy agents, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, antimicrobial agents, cosmetic biocides, antidandruff agents, piroctone olamine, 3,4,4'- trichlorocarbanilide, triclocarban, zinc pyrithione, hydroquinone, kojic acid, ascorbic acid, magnesiuim ascorbyl phosphate, ascorbyl glucoside, pyridoxine, skin-conditioning agents, humectants, occlusive agents, skin soothing agents, skin healing agents, panthenol, panthenol derivatives, ethyl panthenol, aloe vera, terpene alcohols, antioxidants, radical scavengers, pantothenic acid and its derivatives, allantoin, bisabolol, dipotassium glycyrrhizinate, skin treating agents, vitamin D compounds, mono-,di-, and tri-terpenoids, beta-ionol, cedrol, and their derivatives, a glycerol, a sorbitol, a pentaerythritol, a pyrrolidone acid and its salts, dihydroxyacetone, erythrulose, glyceraldehyde, tartaraldehyde, a polysaccharide,an essential fatty acid, a salicylate, a glycyrrhetinic acid, carotenoids, ceramides and pseudo-ceramides, a lipid complex, and combinations thereof.

Further skin care and hair care active ingredients that are particularly useful in combination with the tri/tetrapeptide mixture can be found in SEDERMA commercial literature and on the website www.sederma.fr. (herewith incorporated in its entirety).

In any embodiment of the present invention, however, the additional ingredients useful herein can be categorized by the benefit they provide or by their postulated mode of action. However, it is to be understood that the additional ingredients useful herein can in some instances provide more than one benefit or operate via more than one mode of action. Therefore, classifications herein are made for the sake of convenience and are not intended to limit the additional ingredients to that particular application or applications listed.

1) Farnesol

The topical compositions of the present invention may contain a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7.11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the compositions of the present invention, the composition preferably contains from about 0.001% to about 50%, by weight of the composition, more preferably from about 0.01% to about 20%, even more preferably from about 0.1% to about 15%, even more preferably from about 0.1% to about 10%, still more preferably from about 0.5% to about 5%, and still more preferably from about 1% to about 5% of farnesol.

2) Phytantriol

The topical compositions of the present invention may contain a safe and effective amount of phytantriol. Phytantriol is the common name for the chemical known as 3,7.11.15, tetramethylhexadecane-1,2,3,-triol. Phytantriol is commercially available from BASF (1609 Biddle Avenue, Wyandotte, Mich.). For example, phytantriol is useful as a spider vessel/red blotchiness repair agent, a dark ring/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines. In the compositions of the present invention, the phytantriol is preferably included in an amount from about 0.001% to about 50% by weight of the composition, more preferably from about 0.01% to about 20%, even more preferably from about 0.1% to about 15%, even more preferably from about 0.2% to about 10%, still more preferably from about 0.5% to about 10%, and still more preferably from about 1% to about 5%.

3) Desquamation Actives

A safe and effective amount of a desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to improve the texture of the skin (e.g., smoothness).

One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

4) Enzymes, Enzyme Inhibitors and Enzyme Activators (Co-enzymes)

The compositions of the present invention may contain a safe and effective amount of one or more enzymes, enzyme inhibitors or enzyme activators (coenzymes). Examples of enzymes are lipases, proteases, catalase, superoxide-dismutase, amylases, glucuronidases, peroxidases, in particular glutathione peroxidase or lactoperoxidase, ceramidases, hyaluronidases. All of these enzymes may be obtained by extraction or by fermentation biotechnology processes. Examples of enzyme inhibitors include trypsine inhibitors, Bowmann Birk inhibitor, chymotrypsin inhibitors, botanical extracts with or without tannins, flavonoids, quercetin which inhibit enzymatic activity. Enzyme preparations can be found, for instance, in the product named VENUCEANE™ proposed by SEDERMA, France (WO 02/066668 of Aug. 28, 2002). Enzyme activators and coenzymes include Coenzyme A, coenzyme Q10 (ubiquinone), glycyrrhizidine glycyrrhizine?), berberine, chrysine.

5) Peptides

The compositions of the present invention may also contain peptides including but not limited to, di-, tri-, tetra-, penta- and hexapeptides and derivatives thereof, may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine (beta-Ala-His). Suitable tripeptides for use herein include Arg-Lys-Arg, His-Gly-Gly. Preferred tripeptides and derivatives thereof include N-Palmitoyl-Gly-Lys-His, (which may be purchased from Sederma, France); Peptide CK (Arg-Lys-Arg); Peptide CK+(ac-Arg-Lys-Arg-NH2); and a copper derivative of His-Gly-Gly sold commercially as lamin, from Sigma (St. Louis, Mo.). Suitable tetrapeptides for use herein include Peptide E, Arg-Ser-Arg-Lys (SEQ ID NO:4). Other suitable peptides for use herein include, but are not limited to Tyr-Arg, Val-Trp, Asn-Phe, Asp-Phe, N-Palmitoyl-beta-Ala-His, N-Acetyl-Tyr-Arg-hexadecylester, and derivatives thereof, N-palmitoyl-Gly-Gln-Pro-Arg (SEQ ID NO:1) (from Sederma, France) and derivatives thereof, Lys-Phe-Lys, N-Elaidoyl-Lys-Phe-Lys and its analogs of preservative substitution, N-Acetyl-Arg-¬ Lys-Arg-NH2, and derivatives thereof. Suitable pentapeptides and hexapeptides for use herein include, but are not limited to N-Palmitoyl-Lys-Thr-Thr-Lys-Ser (SEQ ID NO:3), N-Palmitoyl-Tyr-Gly-Gly-Phe-X with X Met or Leu (SEQ ID NO:6) or mixtures thereof, N-Palmitoyl-Val-Gly-Val-Ala-Pro-Gly (SEQ ID NO:7) and derivatives thereof. A preferred dipeptide derivative is N-Acetyl-Tyr-Arg-hexadecylester (CALMOSENSINE™ from SEDERMA, France). Preferred tripeptides and derivatives thereof include N-Palmitoyl-Gly-Lys-His (Pal-GKH from SEDERMA, France), Peptide CK (Arg-Lys-Arg) and Lipospondin (N-Elaidoyl-Lys-Phe-Lys) and its preservative substitution analogs, Peptide CK+ (N-Acetyl-Arg-Lys-Arg-NH2). Suitable pentapeptides for use herein also include N-Palmitoyl-Lys-Thr-Thr-Lys-Ser (SEQ ID NO:3), available as MATRIXYL™ from SEDERMA, France. Hexapeptides such as those disclosed in French Patent Appin. No. FR 0305707, filed May 12, 2003, in the name of SEDERMA may also be used. Compositions containing peptide derivatives useful as an additional ingredient for the present invention are for example, but are not limited to, EYELISS™, MATRIXYL™ 3000 and DERMAXYL™.

When included in the present compositions, the additional peptides are preferably used in amounts of from about 1X10-6% to about 10%, more preferably from about 1X10-6% to about 0.1%, even more preferably from about 1X10-5%-- to about 0.01%, by weight of the composition. In certain embodiments which include the peptide Carnosine™, the compositions preferably contain from about 0.1% to about 5%, by weight of the composition, of such peptides. In other embodiments wherein the peptide-containing composition Biopeptide CL™ is included, the resulting composition preferably contains from about 0.1% to about 10%, by weight of the composition, of the Biopeptide CL™. In the same way the composition can include compositions MATRIXYL™ 3000 and DERMAXYL™. Principal additional peptides according to the present invention include N-Acyl-Gly-His-Lys and N-Acyl-Gly-Gln-Pro-Arg (SEQ ID NO:8) and preferentially, N-Palmitoyl-Gly-His-Lys and N-Palmitoyl-Gly-Gln-Pro-Arg (SEQ ID NO:1). The preferred compositions commercially available containing a tripeptide or a derivative include Biopeptide-CL by SEDERMA, Maxilip™ by SEDERMA, Biobustyl™ by SEDERMA. The compositions commercially available preferred sources of tetrapeptides include RIGIN™, EYELISS™, MATRIXYL™ RELOADED, and MATRIXYL™ 3000 which contain between 50 and 500 ppm of palmitoyl-Gly-Gln-Pro-Arg (SEQ ID NO:1), and carrier, proposed by SEDERMA, France.

6) Botanical Extracts and Marine Extracts

The compositions of the present invention may contain a safe and effective amount of one or more extracts obtained from vegetable or marine sources. These extracts may be obtained by standard extraction processes, and be used in powder, paste, balm, oil, or liquid (i.e., solution) form, preferentially as hydroglycolic extracts of terrestrial plants or marine plants, such as seaweeds, algae, microalgae. These botanical and marine extracts possess various properties well known in cosmetic usage and may be advantageously combined with UGT inducers object of this patent: soothing and anti-inflammatory, enzyme inhibition, moisturizing, anti-wrinkle, hormone replacement, anti-oxidant, emollient, seboregulating, anti-hairloss, hair growth promoting, anti-cellulite, skin healing, skin whitening, lipolytic, tanning, anti-microbial and the like.

7) Anti-Acne Actives

The compositions of the present invention may contain a safe and effective amount of one or more anti-acne actives. Examples of useful anti-acne actives include resorcinol, sulfur, salicylic acid, benzoyl peroxide, erythromycin, zinc, dehydroacetic acid, etc. Further examples of suitable anti-acne actives are described in further detail in U.S. Pat. No. 5,607,980. issued to McAtee et al., on Mar. 4, 1997. Especially useful are combinations with the anti-acne ingredient called Ac.net™ offered by SEDERMA and described in WO 03/028692 A2 of Apr. 10, 2003

8) Anti-Wrinkle Actives/Anti-Atrophy Actives

The compositions of the present invention may further contain a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), keto acid (e.g. pyruvic acid), ascorbic acid (vitamin C), stilbenes, cinnamates, resveratrol, kinetin, dimethylaminoethanol, peptides from natural sources (e.g. soy peptides), salts of sugar acids (e.g., Mn gluconate) phytic acid, lipoic acid; lysophosphatidic acid, skin peel agents (e.g., phenol and the like), vitamin B3 compounds and retinoids which enhance the keratinous tissue appearance benefits of the present invention, especially in regulating keratinous tissue condition, e.g., skin condition, and other vitamin B compounds (e.g., thiamine (vitamin B1), pantothenic acid (vitamin B5), riboflavin (vitamin B2), and their derivatives and salts (e.g., HCL salts or calcium salts)). Especially useful are combinations with the wrinkle agents called Dermolectine™ and Sterocare™ offered by SEDERMA, the latter described in WO99/18927 of Apr. 22, 1999.

(a) Vitamin B3 Compounds

The compositions of the present invention may contain a safe and effective amount of a vitamin B3 compound. Vitamin B3 compounds are particularly useful for regulating skin condition as described in co-pending U.S. application Ser. No. 08/834,010. filed Apr. 11, 1997 (corresponding to international publication WO 97/39733 AI, published Oct. 30, 1997). When vitamin B3 compounds are present in the compositions of the instant invention, the compositions preferably contain from about 0.01% to about 50%, more preferably from about 0.1% to about 10%, even more preferably from about 0.5% to about 10%, and still more preferably from about 1% to about 5%, still more preferably from about 2% to about 5%, by weight of the composition, of the vitamin B3 compound.

As used herein, "vitamin B3 compound" means a compound having the formula:

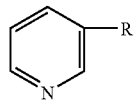

wherein R is _CONH2 (i.e., niacinamide), _COOH (i.e., nicotinic acid) or _CH2OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

Examples of suitable vitamin B3 compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

(b) Retinoids

The compositions of the present invention may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120. issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34.075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate).

Preferred retinoids are retinol, retinyl palmitate, retinyl acetate, retinyl propionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure.

The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%. Where the compositions of the present invention contain both a retinoid and a Vitamin B3 compound, the retinoid is preferably used in the above amounts, and the vitamin B3 compound is preferably used in an amount of from or about 0.1% to or about 10%, more preferably from or about 2% to or about 5%.

9) Hydroxy Acids

The compositions of the present invention may contain a safe and effective amount of a hydroxy acid. Preferred hydroxy acids for use in the compositions of the present invention include salicylic acid and salicylic acid derivatives. When present in the compositions of the present invention, salicylic acid is preferably used in an amount of from about 0.01% to about 50%, more preferably from about 0.1% to about 20%, even more preferably from about 0.1% to about 10%, still more preferably from about 0.5% to about 5%, and still more preferably from about 0.5% to about 2%.

10) Anti-Oxidants/Radical Scavengers

The compositions of the present invention may include a safe and effective amount of an anti-oxidant/radical scavenger or an oxidizer/reducing agent. The anti-oxidant/radical scavenger or oxidizer/reducing agent is especially useful for providing protection against UV radiation which can cause increased scaling or texture changes in the stratum corneum and against other environmental agents which can cause skin damage. These compounds may also be useful in hair drying and other cosmetic applications.

A safe and effective amount of an anti-oxidant/radical scavenger or an oxidizer/reducing agent may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, peroxides including hydrogen peroxide, perborate, thioglycolates, persulfate salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

11) Chelators

The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation.

Examples of chelating agents include N-hydroxysuccinimide, EDTA, NTA, deferoxamine, hydroxamic acids and their salts, phytic acid, phytate, gluconic acid and its salts, transferrine, lactoferrin.

A safe and effective amount of a chelating agent may be added to the compositions of the subject invention, preferably from about 0.00001% to about 10%, more preferably from about 0.001% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are N-hydroxysuccinimide deferoxamine, lactoferrin, hydroxamic acids, gluconic acid, phytic acid, and derivatives thereof 12) Flavonoids The compositions of the present invention may optionally contain flavonoid compound. Flavonoids are broadly disclosed in U.S. Pats. Nos. 5,686,082 and 5,686,367, both of which are herein incorporated by reference. Flavonoids suitable for use in the present invention are one or more flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2.2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4.2',4'-trihydroxy chalcone. 2.2',4'-trihydroxy chalcone, etc.), unsubstituted flavone, 7.2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), genistein (5,7,4'-trihydroxy isoflavone), equol (7-4' dihydroxy isoflavan), 5,7-dihydroxy-4'-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. More preferred are unsubstituted flavanone, unsubstituted chalcone (especially the trans isomer), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.). Mixtures of the above flavonoid compounds may also be used.

The herein described flavonoid compounds are preferably present in the instant invention at concentrations of from about 0.000001% to about 10%, more preferably from about 0.000001% to about 1%, and still more preferably from about 0.0001% to about 0.1% (w/w)

13) Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, fluradrenolone, halcinonide, hydrocortisone acetate, hydrocortisone butyrate, methylprednisolone, triamcinolone acetonide, cortisone, cortodoxone, flucetonide, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used.

The preferred steroidal anti-inflammatory for use is hydrocortisone. A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents. For example, etofenamate, a flufenamic acid derivative, is particularly useful for topical application. Of the nonsteroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are more preferred.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, *Piper methysticum* extract (Kava Kava from SEDERMA, disclosed in FR 2 771 002 of Mar. 31.2000 and WO 99/25369), *Bacopa monieri* extract (Bacocalmine™ from SEDERMA, disclosed in WO 99/40897 of Aug. 19, 1999) and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

14) Anti-Cellulite Agents

The compositions of the present invention may also contain a safe and effective amount of an anti-cellulite agent. Suitable agents may include, but are not limited to, xanthine compounds (e.g., caffeine, theophyliine, theobromine, and aminophylline). Especially useful are combinations with the cellulite/slimming agents called Vexel™ (FR 2 654 619 of Jan. 31, 1992), Coaxel (FR 2 694 195 of Jul. 30, 1992), Cycolipase™ (FR 2 733 149 of Apr. 21, 1995), Pleurimincyl™ and Lipocare™ (WO 98/43607 of Oct. 8, 1998) and Unislim™ (FR 0306063 of May 20, 2003), all offered by SEDERMA.

15) Topical Anesthetics

The compositions of the present invention may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

16) Tanning Actives

The compositions of the present invention may contain a tanning active. When present, it is preferable that the compositions contain from about 0.1% to about 20%, more preferably from about 2% to about 7%, and still more preferably from about 3% to about 6%, by weight of the composition, of dihydroxyacetone as an artificial tanning active.

Dihydroxyacetone, which is also known as DHA or 1,3-dihydroxy-2-propanone, is a white to off-white, crystalline powder. This material can be represented by following chemical structure.

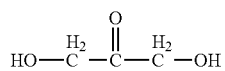

The compound can exist as a mixture of monomers and dimers, with the dimers predominanting in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See The Merck Index, Tenth Edition, entry 3167, p. 463 (1983), and "Dihydroxyacetone for Cosmetics," E. Merck Technical Bulletin, 03-304 110. 319 897, 180 588. Especially useful are combinations with the tanning agents called Tyr-ol and Tyr-exel™ offered by SEDERMA and described in Fr 2 702 766 of Mar. 15, 1993 and WO 03/017966 A2 of Mar. 6, 2003 respectively 17) Skin Lightening Agents The compositions of the present invention may contain a skin lightening agent. When used, the compositions preferably contain from about 0.01% to about 10%, more preferably from about 0.02% to about 5%, also preferably from about 0.05% to about 2%, by weight of the composition, of a skin lightening agent. Suitable skin lightening agents include those known in the art, including kojic acid, arbutin, tranexamic acid, ascorbic acid and derivatives thereof (e.g., magnesium ascorbyl phosphate or sodium ascorbyl phosphate, ascorbyl glucoside and the like), and extracts (e.g., mulberry extract, placental extract). Skin lightening agents suitable for use herein also include those described in the PCT publication No. 95/34280. in the name of Hillebrand, corresponding to PCT Application No. U.S. Ser. No. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication Ser. No. 95/23780. published Sep. 8, 1995. Especially useful are combinations with the skin lightening agents called Melaclear™, Etioline™, Melaslow™ and Lumiskin™ offered by SEDERMA and described respectively in FR 2 732 215 of Mar. 28, 1995, WO 98/05299 of Aug. 2, 1996, WO 02/15871 of Feb. 28, 2002 and PCT/FR 03/02400 of Aug. 30, 2002.

Other skin lightening materials suitable for use herein include Acitwhite&commat® (Cognis), Emblica&commat® (Rona), Azeloglinica® (Sinerga), and Sepiwhite®® (Seppic)

18) Skin Soothing and Skin Healing Actives

The compositions of the present invention may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed. Especially useful are combinations with the skin soothing and healing agents called Calmosensine™ and Bacocalmine™ offered by SEDERMA and described in WO 98/07744 of Feb. 26, 1998 and WO 99/40897 of Aug. 19, 1999 respectively.

19) Bisabolol

The topical compositions of the present invention may also contain a safe and effective amount of bisabolol. Bisabolol is a naturally occurring unsaturated monocyclic terpene alcohol having the following structure

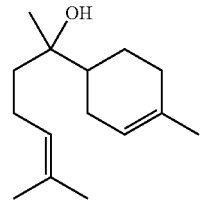 [SMILES: CC(C)=CCCC(C)(O)C1CC=C(C)CC1]

It is the primary active component of chamomile extract/oil. Bisabolol can be synthetic (d.1-alpha-isomer or (+/−)-alpha-isomer) or natural ((−)-alpha-isomer) in origin and can be used as essentially pure compounds or mixtures of compounds (e.g., extracts from natural sources such as chamomile). The alpha form of bisabolol (a-bisabolol) is used in a variety of cosmetic products as a skin conditioning or soothing agent. As used herein, "bisabolol" includes chamomile extract or oil and any isomers and tautomers of such. Suitable bisabolol compounds are commercially available as a natural material from Dragoco (Totowa, N.J.) under the product name alpha-bisabolol natural and as a synthetic material from Fluka (Milwaukee, Wis.) under the product name alpha-bisabolol. In the compositions of the present invention, the composition preferably contains from about 0.001% to about 50%, by weight of the composition, more preferably from about 0.01% to about 20%, even more preferably from about 0.01% to about 15%, and still more preferably from about 0.1% to about 10%, of bisabolol, even more preferably from about 0.1% to about 5%.

20) Antimicrobial and Antifungal Actives

The compositions of the present invention may contain an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and still more preferably from about 0.05% to about 2%. Especially useful are combinations with the ingredient range called OSMOCIDE™ offered by SEDERMA and described in WO 97/05856 of Feb. 20, 1997.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, miconazole, ketoconazole, neocycin sulfate, and mixtures thereof.

21) Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2.2',4,4'-tetrahydroxybenzophenone, 2.2'-dihydroxy-4, 4'-dimethoxybenzophenone, octabenzone; 4-isopropyldibenzoylmethane; butylmethoxydibenzoylmethane; etocrylene; octocrylene; [3-(4'-methylbenzylidene boman-2-one), terephthalylidene dicamphor sulfonic acid and 4-isopropyl-di-benzoylmethane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyidimethyl-p-aminobenzoic acid, digalloyltrioleate, 2.2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethyl-aminobenzoate, 2-phenylbenzimidazole-5-sulfonic acid, 2-(p-dimethylaminophenyl)-5-sulfonicbenzoxazoic acid, octocrylene, zinc oxide, titanium oxide, and mixtures of these compounds, are preferred.

Also preferred are the compositions and combinations described and claimed in U.S. Pat. No. 6,190,645 to SaNogueira et al. and in particular, sunscreen agents disclosed at col. 3, Ins. 4-23, in combination with a cinnamido alkyl amine cationic quaternary salt such as cinnamidopropyl trimethyl ammonium chloride sold under the trademark INCROQUAT-UV-283 manufactured by Croda, Inc., 7 Century Road, Parsippany, N.J. These portions of the U.S. Pat. No. 6,190,645 are hereby incorporated by reference. More preferred organic sunscreen actives useful in the compositions useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyidimethyl-p-aminobenzoicacid, octocrylene and mixtures thereof.

Also particularly useful in the compositions are sunscreen actives such as those disclosed in U.S. Pat. No. 4,937,370 issued to Sabatelli on Jun. 26, 1990. and U.S. Pat. No. 4,999, 186 issued to Sabatelli & Spirnak on Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof.

Especially preferred sunscreen actives include 4,4'-t-butyl-methoxydibenzoylmethane, 2-ethylhexyl-p-methoxycinnamate, phenyl benzimidazole sulfonic acid, and octocrylene.

A safe and effective amount of the organic sunscreen active is used, typically from about 1% to about 20%, more typically from about 2% to about 10% by weight of the composition. Exact amounts will vary depending upon the sunscreen or sunscreens chosen and the desired Sun Protection Factor (SPF).

22) Particulate Material

The compositions of the present invention may contain a particulate material, preferably a metallic oxide. These particulates can be coated or uncoated, charged or uncharged. Charged particulate materials are disclosed in U.S. Pat. No. 5,997,887, to Ha et al., incorporated herein by reference. Particulate materials useful herein include: bismuth oxychloride, iron oxide, mica, mica treated with barium sulfate and TiO2, zeolite, kaolin, boron nitride, lauroyl lysine, nylon, polystyrene, PFTE, silica, nylon, polyethylene, talc, styrene, polyproylene, ethylene/acrylic acid copolymer, sericite, aluminum oxide, silicone resin, barium sulfate, calcium carbonate, cellulose acetate, titanium dioxide, polymethyl methacrylate, starch, modified starches such as aluminum starch octenyl succinate, silk, glass and mixtures thereof.

Inorganic particulate materials, e.g., TiO2, ZnO, or ZrO2 are commercially available from a number of sources. One example of a suitable particulate material contains the material available from U.S. Cosmetics (TRONOX TiO2 series, SAT-T CR837, a rutile TiO2). Preferably, particulate materials are present in the composition in levels of from about 0.01% to about 2%, more preferably from about 0.05% to about 1.5%, still more preferably from about 0.1% to about 1%, by weight of the composition.

23) Conditioning Agents

The compositions of the present invention may contain a conditioning agent selected from humectants, moisturizers, or skin conditioners. A variety of these materials can be employed and each can be present at a level of from about 0.01% to about 20%, more preferably from about 0.1% to about 10%, and still more preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; petrolaum and mixtures thereof. Also useful herein are the propoxylated glycerols described in U.S. Pat. No. 4,976,953, to Orr et al., issued Dec. 11, 1990.

Also useful are various C1-C30 monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300. to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360. to Volpenhein, issued May 21, 1985.

Preferably, the conditioning agent is selected from urea, guanidine, sucrose polyester, panthenol, dexpanthenol, allantoin, and combinations thereof.

24) Water-soluble Vitamins

The compositions of the present invention may contain a safe and effective amount of one or more water-soluble vitamins. Examples of water-soluble vitamins include, but are not limited to, water-soluble versions of vitamin B, vitamin B derivatives, vitamins $B_1$ through $B_{12}$, and theirs derivatives, vitamin C, vitamin C derivatives, vitamin H, vitamin K, vitamin K derivatives, vitamin D, vitamin D derivatives, vitamin E, vitamin E derivatives, and mixtures thereof. The vitamin compounds may be included as the substantially pure material, or as an extract obtained by suitable physical and/or chemical isolation from natural (e.g., plant) sources. When vitamin compounds are present in the compositions of the instant invention, the compositions preferably contain from about 0.0001% to about 50%, more preferably from about 0.001% to about 10%, still more preferably from about 0.01% to about 5%, and still more preferably from about 0.1% to about 5%, by weight of the composition, of the vitamin compound.

25) Structuring Agents

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more preferably from about 0.1% to about 10%, still more preferably from about 0.5% to about 9%, of one or more structuring agents.

Preferred structuring agents are those having an HLB of from about 1 to about 8 and having a melting point of at least about 45° C. Suitable structuring agents are those selected from saturated C14 to C30 fatty alcohols, saturated C16 to C30 fatty alcohols containing from about 1 to about 5 moles of ethylene oxide, saturated C16 to C30 diols, saturated C16 to C30 monoglycerol ethers, saturated C16 to C30 hydroxy fatty acids, C14 to C30 hydroxylated and nonhydroxylated saturated fatty acids, C14 to C30 saturated ethoxylated fatty acids, amines and alcohols containing from about 1 to about 5 moles of ethylene oxide diols, C14 to C30 saturated glyceryl mono esters with a monoglyceride content of at least 40%, C14 to C30 saturated polyglycerol esters having from about 1 to about 3 alkyl group and from about 2 to about 3 saturated glycerol units, C14 to C30 glyceryl mono ethers, C14 to C30 sorbitan mono/diesters, C14 to C30 saturated ethoxylated sorbitan mono/diesters with about 1 to about 5 moles of ethylene oxide, C14 to C30 saturated methyl glucoside esters, C14 to C30 saturated sucrose mono/diesters, C14 to C30 saturated ethoxylated methyl glucoside esters with about 1 to about 5 moles of ethylene oxide, C14 to C30 saturated polyglucosides having an average of between 1 to 2 glucose units and mixtures thereof, having a melting point of at least about 45° C.

The preferred structuring agents of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

26) Thickening Agent (Including Thickeners and Gelling Agents)

The compositions of the present invention can contain one or more thickening agents, preferably from about 0.1% to about 5%, more preferably from about 0.1% to about 4%, and still more preferably from about 0.25% to about 3%, by weight of the composition.

Nonlimiting classes of thickening agents include those selected from the following:

a) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in CTFA International Cosmetic Ingredient Dictionary, Ninth Edition, 2002.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b) Crosslinked Polyacrylate Polymers

The compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660. to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

c) Polyacrylamide Polymers

The compositions of the present invention can optionally contain polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. (Paterson, N.J.).

Ready-Made Gels

The compositions may also contain thickening and texturising gels of the type as exemplified by the product range called Lubrajel® from United Guardian, 230 Marcus Blvd, Hauppauge N.Y. 11788. These gels have moisturizing, viscosifying, stabilizing properties and may be used in concentration ranges between 1 and 99%, most advantageously between 5 and 15%.

d) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkyl-celluloses. Examples of alkyl groups useful herein include those selected from stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.). Other useful polysaccharides include scleroglucans which are a linear chain of (1-3) linked glucose units with a (1-6) linked glucose every three units, a commercially available example of which is Clearogel™ CS11 from Michel Mercier Products Inc. (Mountainside, N.J.).

e) Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Preferred compositions of the present invention include a thickening agent selected from carboxylic acid polymers, crosslinked polyacrylate polymers, polyacrylamide polymers, and mixtures thereof, more preferably selected from carboxylic acid polymers, polyacrylamide polymers, and mixtures thereof.

27) Dermatologically-Acceptable Carrier

The compositions of the invention may be used in various cosmetic and/or personal care products, for example, skin care, hair care, nail care, facial and body care and sunscreen compositions, such as lotions, gels, sprays, and the like, hand cleaners, bath compositions, suntan oils, antiperspirant compositions, Fragrances and colognes, cold creams, hair sunscreen compositions, pre-shaves, deodorants, topical pharmaceutical ointments, skin moisturizers, facial cleansers, cleansing creams, skin gels, shampoos, hair conditioners, detergents, household cleaning products, make-up products, lipstick products, mascara, and hair coloring products. Therefore, in addition to any of the above cited skin care or hair care peptides and other actives, the cosmetic compositions described in the present invention may often include as an additional ingredient a dermatologically acceptable carrier. The form of the carrier and the final product resulting from the combination of the tetrapeptides with any additional active and with the carrier may be any of the following: liquids, gels, creams, water-in-oil and oil-in-water, and silicone emulsions, foams, and solids; they may be clear or opaque; and may be formulated as both aqueous and non-aqueous preparations, including but not limited to topical preparations.

To realize the invention in any of these physical forms, further substances, agents and compounds are useful although not always necessary such as Conditioning Agents, Structuring Agents and Thickening Agents. These compounds sometimes also have the role of adjuvant and sometimes the role of additional ingredient. Neither role excludes them from the present invention as being combined with the tetrapeptide/tripeptide mixtures of the invention and their derivatives.

The nature of the dermatologically acceptable carrier, the nature of the final product, and the methods of preparing those need not be described here in detail; many examples can be found in the available literatures, such as PCT application No. WO 00/62743 filed by Larry R. Robinson et al. on Apr. 19, 2000. published on Oct. 26, 2000. or, more generally, in Milady's Standard Textbook of Cosmetology 2000. (Delmar Learning) or in Formulation Technology: Emulsions, Suspensions, Solid Forms by Hans Mollet, Arnold Grubenmann and Helen Payne, published by John Wiley & Sons (Jan. 23, 2001), or in Chemistry and Technology of the Cosmetics and Toiletries Industry by Clifford Williams Schmitt, Kluwer Academic Publishers, Dordrecht July 1996, all hereby incorporated. Fiedler's Encyclopedia of Excipients, fifth edition, Edition Cantor Verlag Aulendorf, 2002 is also a useful guide for the formulator skilled in the art of developing cosmetic carriers. All ingredients listed therein may in one way or another be combined to form a dermatologically acceptable carrier and/or used as an additional ingredient for the cosmetic compositions of the invention.

In most instances, the additional ingredients will include a dermatologically acceptable carrier either alone or in combination with still other additional ingredients. The amounts of additional ingredients may range from about 99.5% to about 99.99999%, preferably from about 99.9% to about 99.9999%, more preferably from about 99.99% to about 99.999%, of the composition. In short, it is the balance of the composition. If carriers (either singularly, such as water, or complex cosolvents) are used, they may make up the entire balance of the compositions.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions. As will be understood by the skilled artisan, a given component will distribute primarily into either the water or oil/silicone phase, depending on the water solubility/dispersibility of the component in the composition. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560. issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Preferred water-in-silicone and oil-in-water emulsions are described in greater detail below.

A) Water-in-Silicone Emulsion

Water-in-silicone emulsions contain a continuous silicone phase and a dispersed aqueous phase.

(1) Continuous Silicone Phase

Preferred water-in-silicone emulsions of the present invention contain from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for the retinoid. The continuous silicone phase of these preferred emulsions contain between about 50% and about 99.9% by weight of organopolysiloxane oil and less than about 50% by weight of a non-silicone oil. In an especially preferred embodiment, the continuous silicone phase contains at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and even more preferably less than about 2%, by weight of the continuous silicone phase. These preferred emulsion systems provide more oxidative stability to the retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in PCT Application WO 97/21423, published Jun. 19, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1.000.000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10.000. chosen to achieve the desired molecular weight which can range to over about 10.000.000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50. 350. and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10.000.000. Examples of these alkyl-substituted dimethicones include cetyl dimethicone and lauryl dimethicone.

Cyclic polyalkylsiloxanes suitable for use in the composition include those represented by the chemical formula $[SiR_2\_O]_n$ wherein R is an alkyl group (preferably R is methyl or ethyl, more preferably methyl) and n is an integer from about 3 to about 8, more preferably n is an integer from about 3 to about 7, and still more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500. chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of the selected retinoid in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(2) Dispersed Aqueous Phase

The topical compositions of the present invention contain from about 30% to about 90%, more preferably from about 50% to about 85%, and still more preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such ingredients include thickeners, acids, bases, salts, chelants, gums, water-soluble or dispersible alcohols and polyols, buffers, preservatives, sunscreening agents, colorings, and the like.

The topical compositions of the present invention will typically contain from about 25% to about 90%, preferably from about 40% to about 80%, more preferably from about 60% to about 80%, water in the dispersed aqueous phase by weight of the composition.

(3) Emulsifier for Dispersing the Aqueous Phase

The water-in-silicone emulsions of the present invention preferably contain an emulsifier. In a preferred embodiment, the composition contains from about 0.1% to about 10% emulsifier, more preferably from about 0.5% to about 7.5%, still more preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with components of the composition of the present invention, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and still more preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

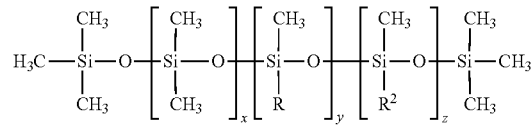

wherein R is C1-C30 straight, branched, or cyclic alkyl and R2 is selected from the group consisting of

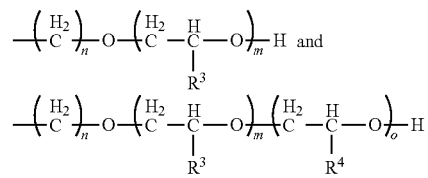

wherein n is an integer from 3 to about 10; R3 and R4 are selected from the group consisting of H and C1-C6 straight or branched chain alkyl such that R3 and R4 are not simultaneously the same; and m, o, x, and y are selected such that the molecule has an overall molecular weight from about 200 to about 10.000.000. with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the R2 moieties containing the R3 and R4 groups are not meant to be limiting but are shown as such for convenience.

Also useful herein, although not strictly classified as dimethicone copolyols, are silicone surfactants as depicted in the structures in the previous paragraph wherein R2 is: _(CH2)n_O_R5, wherein R5 is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190. 193, Q2-5220. 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt).

Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See International Cosmetic Ingredient Dictionary, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330.369, to SanoGueira, published Aug. 30, 1989; G. H. Dahms, et al., "New Formulation Possibilities Offered by Silicone Copolyols," Cosmetics & Toiletries, vol. 110. pp. 91-100. March 1995; M. E. Carlotti et al., "Optimization of W/O-S Emulsions And Study Of The Quantitative Relationships Between Ester Structure And Emulsion Properties," J. Dispersion Science And Technology, 13(3), pp. 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," Provisional Communication International Journal of Cosmetic Science, 12, pp. 135-139 (1990); and D. G. Krzysik et al., "A New Silicone Emulsifier For Water-in-Oil Systems," Drug and Cosmetic Industry, vol. 146(4) pp. 28-81 (April 1990).

Among the non-silicone-containing emulsifiers useful herein are various nonionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicon-containing emulsifiers include: polyethylene glycol 20 sorbitan monolaurate (Polysorbate 20), polyethylene glycol 5 soya sterol, Steareth-20. Ceteareth-20. PPG-2 methyl glucose ether distearate, Ceteth-10. Polysorbate 80. cetyl phosphate, potassium cetyl phosphate, diethanolamine cetyl phosphate, Polysorbate 60. glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20. ceteareth-20. PPG-2 methyl glucose ether distearate, ceteth-10. diethanolamine cetyl phosphate, glyceryl stearate, PEG-100 stearate, and mixtures thereof.

B) Oil-in-Water Emulsions

Other preferred topical carriers include oil-in-water emulsions, having a continuous aqueous phase and a hydrophobic, water-insoluble phase ("oil phase") dispersed therein. Examples of suitable oil-in-water emulsion carriers are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(1) Structuring Agent

A preferred oil-in-water emulsion contains a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention contain from about 0.5% to about 20%, more preferably from about 1% to about 10%, even more preferably from about 1% to about 5%, by weight of the composition, of a structuring agent.

The preferred structuring agents of the present invention include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, steareth-21, and mixtures thereof.

(2) Hydrophilic Surfactant

The preferred oil-in-water emulsions contain from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water.

Preferred hydrophilic surfactants are selected from nonionic surfactants. Among the nonionic surfactants that are useful herein are those that can be broadly defined as condensation products of long chain alcohols, e.g. C8-C30 alcohols, with sugar or starch polymers, i.e., glycosides. These compounds can be represented by the formula (S)n_O_R wherein S is a sugar moiety such as glucose, fructose, mannose, and galactose; n is an integer of from about 1 to about 1000. and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-C20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula RCO(X)nOH wherein R is a C10-C30 alkyl group, X is _OCH2CH2_ (i.e. derived from ethylene glycol or oxide) or _OCH2CH(CH$_3$)_ (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula RCO(X)nOOCR wherein R is a C10-C30 alkyl group, X is _OCH2CH2_ (i.e. derived from ethylene glycol or oxide) or _OCH2CH(CH3)_ (i.e. derived from propylene glycol or oxide), and n is an integer from about 6 to about 100. Other nonionic surfactants are the condensation products of alkylene oxides with fatty alcohols (i.e. alkylene oxide ethers of fatty alcohols). These materials have the general formula R(X)nOR' wherein R is a C10-C30 alkyl group, X is _OCH2CH2_ (i.e., derived from ethylene glycol or oxide) or _OCH2CH(CH3)_ (i.e., derived from propylene glycol or oxide), and n is an integer from about 6 to about 100 and R' is H or a C10-C30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula RCO(X)n OR' wherein R and R' are C10-C30 alkyl groups, X is _OCH2CH2_ (i.e., derived from ethylene glycol or oxide) or _OCH2CH(CH3)_ (derived from propylene glycol or oxide), and n is an integer from about 6 to about 100. Nonlimiting examples of these alkylene oxide derived nonionic surfactants include ceteth-6, ceteth-10. ceteth-12, ceteareth-6, ceteareth-10. ceteareth-12, steareth-6, steareth-10. steareth-12, steareth-21, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

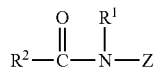

wherein: R1 is H, C1-C4 alkyl, 2-hydroxyethyl, 2-hydroxypropyl, preferably C1-C4 alkyl, more preferably methyl or ethyl, most preferably methyl; R2 is C5-C31 alkyl or alkenyl, preferably C7-C19 alkyl or alkenyl, more preferably C9-C17 alkyl or alkenyl, most preferably C11-C15 alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R2CO_ moiety is derived from coconut oil fatty acids). Processes for making compositions containing polyhydroxy fatty acid amides are disclosed, for example, in G.B. Patent Specification 809.060. published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Preferred among the nonionic surfactants are those selected from the group consisting of steareth-21, ceteareth-20. ceteareth-12, sucrose cocoate, steareth-100. PEG-100 stearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these emulsifiers include: polyethylene glycol 20 sorbitan monolaurate (Polysorbate 20), polyethylene glycol 5 soya sterol, Steareth-20. Ceteareth-20. PPG-2 methyl glucose ether distearate, Ceteth-10. Polysorbate 80. cetyl phosphate, potassium cetyl phosphate, diethanolamine cetyl phosphate, Polysorbate 60. glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Another group of non-ionic surfactants useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate. This is commercially available from ICI under the trade name Arlatone 2121.

Other suitable surfactants useful herein include a wide variety of cationic, anionic, zwitterionic, and amphoteric surfactants such as are known in the art and discussed more fully below. See, e.g., McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety. The hydrophilic surfactants useful herein can contain a single surfactant, or any combination of suitable surfactants. The exact surfactant (or surfactants) chosen will depend upon the pH of the composition and the other components present.

Also useful herein are cationic surfactants, especially dialkyl quaternary ammonium compounds or "quats", examples of which are described in U.S. Pat. Nos. 5,151,209; 5,151,210; 5,120,532; 4,387,090; 3,155,591; 3,929,678; 3,959,461; McCutcheon's Detergents & Emulsifiers, (North American edition 1979) M.C. Publishing Co.; and Schwartz, et al., Surface Active Agents, Their Chemistry and Technology, New York: Interscience Publishers, 1949; which descriptions are incorporated herein by reference. The cationic surfactants useful herein include cationic ammonium salts such as those having the formula:

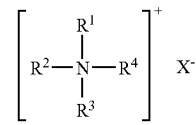

wherein R1, is an alkyl group having from about 12 to about 30 carbon atoms, or an aromatic, aryl or alkaryl group having from about 12 to about 30 carbon atoms; R2, R3, and R4 are independently selected from hydrogen, an alkyl group having from about 1 to about 22 carbon atoms, or aromatic, aryl or alkaryl groups having from about 12 to about 22 carbon atoms; and X is any compatible anion, preferably selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups of R1, R2, R3, and R4 can also contain ester and/or ether linkages, or hydroxy or amino group substituents (e.g., the alkyl groups can contain polyethylene glycol and polypropylene glycol moieties).

More preferably, R1 is an alkyl group having from about 12 to about 22 carbon atoms; R2 is selected from H or an alkyl group having from about 1 to about 22 carbon atoms; R3 and R4 are independently selected from H or an alkyl group having from about 1 to about 3 carbon atoms; and X is as described previously.

Still more preferably, R1 is an alkyl group having from about 12 to about 22 carbon atoms; R2, R3, and R4 are selected from H or an alkyl group having from about 1 to about 3 carbon atoms; and X is as described previously.

Alternatively, other useful cationic emulsifiers include amino-amides, wherein in the above structure R1 is alternatively R5CONH_(CH2)$_n$, wherein R5 is an alkyl group having from about 12 to about 22 carbon atoms, and n is an integer from about 2 to about 6, more preferably from about 2 to about 4, and still more preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C30 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Still more preferred cationic surfactants are those selected from behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula RCO_OCH2CH2SO3M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO3M and RO(C2H4O)xSO3M, wherein R is alkyl or alkenyl of from about 10 to about 30 carbon atoms, x is from about 1 to about 10. and M is a water-soluble cation such as ammonium, sodium, potassium and triethanolamine. Another suitable class of anionic surfactants are the water-soluble salts of the organic, sulfuric acid reaction products of the general formula:

wherein R1 is chosen from the group including a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates of the formulas RN[CH2)mCO2M]2 and RNH(CH2)mCO2M wherein m is from 1 to 4, R is a C8-C22 alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Other amphoteric or zwitterionic surfactants useful herein include betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Miratine CBS from Rhone-Poulenc), and the alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

When the surfactant used is a quaternary nitrogen containing compound ("quat") or indeed when a quat material is used in compositions or products in accordance with preferred embodiments of the invention, cationic activity may be used as a measure of the amount of quat actually used.

Cationic activity is appropriate for discussion in the context of quats. Cationic activity may be measured by several methods readily understood by those skilled in the art. One such method utilizes a standardized solution of an anionic material, such as sodium lauryl sulfate. This material is added to the solution containing the quat until full complexation of the quat's cations (the end point) has been reached. The end point can be measured potentiometrically or by the use of color indicators.

Typical tests involve titrating a sample of the quat, usually dissolved in a solvent, with the standardized solution of sodium lauryl sulfate until the endpoint is reached. As described in the co-pending and co-assigned U.S. patent application Ser. No. 09/438,631, incorporated by reference herein in its entirety, once the endpoint is reached, the cationic activity can be calculated according to the following formula:

$$\% \text{ cationic activity} = \frac{mL \times N \times MW \times 100}{S.wt. \times 1000}$$

Where: mL=the number of mL of anionic material
N=the normality of the solution used
MW=the equivalent molecular weight of the quat being analyzed
S.wt.=the sample weight in grams For additional information regarding the methodology for measuring the cationic activity, see W. Schempp and H. T. Trau, Wochenblatt fur Papierfabrikation 19, 1981, pages 726-732, or J. P. Fischer and K. Lohr, Organic Coatings Science Technology, Volume 8, pages 227-249, Marcel Dekker, Inc. April 1986), both incorporated herein by reference in their entirety. While the use of quat raw materials having a high cationic activity is preferred (activity of at least about 35%, more preferably at least about 50%), use of lower cationic activities are also contemplated, particularly in finished products where the overall cationic activity may be less than 25%, less than 10% and even less than 5%.

(3) Water

The preferred oil-in-water emulsion contains from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may contain a dermatologically acceptable emollient. Such compositions preferably contain from about 1% to about 50% of the emollient. As used herein, "emollient" refers to a material useful for the prevention or relief of dryness, as well as for the protection of the skin. A wide variety of suitable emollients are known and may be used herein. Sagarin, Cosmetics Science and Technology, 2nd Edition, Vol. 1, pp. 32-43 (1972), incorporated herein by reference, contains numerous examples of materials suitable as an emollient. A preferred emollient is glycerin. Glycerin is preferably used in an amount of from or about 0.001 to or about 30%, more preferably from or about 0.01 to or about 20%, still more preferably from or about 0.1 to or about 10%, e.g., 5%.

Examples of suitable emollients include C8-C30 alkyl esters of C8-C30 carboxylic acids; C1-C6 diol monoesters and diesters of C8-C30 carboxylic acids; monoglycerides, diglycerides, and triglycerides of C8-C30 carboxylic acids, cholesterol esters of C8-C30 carboxylic acids, cholesterol, and hydrocarbons. Examples of these materials include diisopropyl adipate, isopropyl myristate, isopropyl palmitate, ethylhexyl palmitate, isodecyl neopentanoate, C12-15 alcohols benzoates, diethylhexyl maleate, PPG-14 butyl ether, PPG-2 myristyl ether propionate, cetyl ricinoleate, cholesterol stearate, cholesterol isostearate, cholesterol acetate, jojoba oil, cocoa butter, shea butter, lanolin, lanolin esters, mineral oil, petrolatum, and straight and branched C16-C30 hydrocarbons.

Also useful are straight and branched chain fatty C8-C30 alcohols, for example, stearyl alcohol, isostearyl alcohol, ethenyl alcohol, cetyl alcohol, isocetyl alcohol, and mixtures thereof. Examples of other suitable emollients are disclosed in U.S. Pat. No. 4,919,934; which is incorporated herein by reference in its entirety. Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof. Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Examples of suitable alkoxylated diesters and trimesters are disclosed in U.S. Pat. Nos. 5,382,377, 5,455,025 and 5,597,555, assigned to Croda Inc., and incorporated herein by reference.

Suitable lipids include C8-C20 alcohol monosorbitan esters, C8-C20 alcohol sorbitan diesters, C8-C20 alcohol sorbitan triesters, C8-C20 alcohol sucrose monoesters, C8-C20 alcohol sucrose diesters, C8-C20 alcohol sucrose triesters, and C8-C20 fatty alcohol esters of C2-C62-hydroxy acids. Examples of specific suitable lipids are sorbitan diisostearate, sorbitan dioleate, sorbitan distearate, sorbitan isostearate, sorbitan laurate, sorbitan oleate, sorbitan palmitate, sorbitan sesquioleate, sorbitan sesquistearate, sorbitan stearate, sorbitan triisostearate, sorbitan trioleate, orbitan tristearate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearate, sorbitan dilaurate, sorbitan stearate, sorbitan laurate, sucrose laurate, sucrose dilaurate, sodium isostearyl lactylate, lauryl pidolate, PPG-14 butyl ether, PPG-15 stearyl ether, and mixtures thereof.

Lotions and creams according to the present invention generally contain a solution carrier system and one or more emollients. Lotions and creams typically contain from about 1% to about 50%, preferably from about 1% to about 20%, of emollient; from about 50% to about 90%, preferably from about 60% to about 80% of water; and the tetrapeptide and tripeptide mixture and the optional additional skin care active (or actives) in the above described amounts. Creams are generally thicker than lotions due to higher levels of emollients or higher levels of thickeners.

Ointments of the present invention may contain a simple carrier base of animal or vegetable oils or semi-solid hydrocarbons (oleaginous); absorption ointment bases which absorb water to form emulsions; or water soluble carriers, e.g., a water soluble solution carrier. Ointments may further contain a thickening agent, such as described in Sagarin, Cosmetics, Science and Technology, 2nd Edition, Vol. 1, pp. 72-73 (1972), incorporated herein by reference, and/or an emollient. For example, an ointment may contain from about 2% to about 10% of an emollient; from about 0.1% to about 2% of a thickening agent; and the tetrapeptide and tripeptide mixture and the optional additional skin care active (or actives) in the above described amounts.

Compositions of this invention useful for cleansing ("cleansers") are formulated with a suitable carrier, e.g., as described above, and preferably contain, in addition to the tetrapeptide and tripeptide mixture and the optional additional skin care active (or actives) in the above described amounts, from about 1% to about 90%, more preferably from about 5% to about 10%, of a dermatologically acceptable surfactant. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20. sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in McCutcheon's Detergents and Emulsifiers, North American Edition (1986), published by Allured Publishing Corporation. The cleansing compositions can optionally contain, at their art-established levels, other materials which are conventionally used in cleansing compositions.

The physical form of the cleansing compositions is not critical. The compositions can be, for example, formulated as toilet bars, liquids, shampoos, bath gels, hair conditioners, hair tonics, pastes, or mousses. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

As used herein, the term "foundation" refers to a liquid, semi-liquid, semi-solid, or solid skin cosmetic which includes, but is not limited to lotions, creams, gels, pastes, cakes, and the like. Typically the foundation is used over a large area of the skin, such as over the face, to provide a particular look. Foundations are typically used to provide an adherent base for color cosmetics such as rouge, blusher, powder and the like, and tend to hide skin imperfections and impart a smooth, even appearance to the skin. Foundations of the present invention include a dermatologically acceptable carrier and may include conventional ingredients such as oils, colorants, pigments, emollients, fragrances, waxes, stabilizers, and the like. Exemplary carriers and such other ingredients which are suitable for use herein are described, for example, in PCT Application, WO 96/33689, to Canter, et al., published on Oct. 31, 1996 and U.K. Patent, GB 2274585, issued on Aug. 3, 1994.

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic.

Examples of anionic monomers include unsaturated carboxylic acid monomers such as acrylic acid, methacrylic acid, maleic acid, maleic acid half ester, itaconic acid, fumeric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyltriethylammonium bromide; amine derivatives of methacrylic acid or amine derivatives of methacrylamide derived from methacrylic acid or methacrylamide and a dialkylalkanolamine having C1-C6 alkyl groups such as dimethylaminoethyl (meth)acrylate, diethylaminoethyl(meth)acrylate, dimethylaminopropyl(meth)acrylate, or dimethylaminopropyl(meth)acrylamide.

Examples of the amphoteric monomers include zwitterionized derivatives of the aforementioned amine derivatives of (meth)acrylic acids or the amine derivatives of (meth)acrylamide such as dimethylaminoethyl(meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth)acrylic acid or (meth) acrylamide, as discussed above, modified with propanesultone.

Examples of nonionic monomers are acrylic or methacrylic acid esters of C1-C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene, chlorostyrene, vinyl esters such as vinyl acetate, vinyl chloride, vinylidene chloride, acrylonitrile, alpha-methylstyrene, t-butylstyrene, butadiene, cyclohexadiene, ethylene, propylene, vinyl toluene, alkoxyalkyl(meth)acrylate, methoxy ethyl(meth)acrylate, butoxyethyl(meth)acrylate, allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl(meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

The compositions of the invention may also include a wide range of miscellaneous ingredients. Some suitable miscellaneous ingredients commonly used in the cosmetic and personal care industry are described in The CTFA Cosmetic Ingredient Handbook, (9th Ed., 2002), which is incorporated by reference herein. These ingredients will be used in amounts which are conventional.

A particularly advantageous composition according to the present invention combines a UGT-inducer (chrysin-), an iron-chelating agent (N-hydroxysuccinimide) and at least one peptide (e.g. N-Palmitoyl-Gly-Gln-Pro-Arg (SEQ ID NO:1) and/or N-Palmitoyl-Gly-His-Lys-) to treat circles under the eyes. In a preferred embodiment the iron-chelating agent and the peptide are present at concentration from about 0.000001% (w/w) to about 10% (w/w), preferably from about 0.00001 (w/w) to about 1% (w/w) and most preferably from about 0.0001% (w/w) to 0.1% (w/w) by weight of the composition.

Compositions

The physical form of the compositions according to the invention is not important: creams, lotions, ointments, gels, emulsions, dispersions, solutions, suspensions, cleansers, foundations, anhydrous preparations (sticks, in particular lipsticks, body and bath oils), emolient lotion, emollient milk, emollient cream, milk for care of the skin or hair, cream for care of the skin or hair shower and bath gels and washes, shampoos and scalp treatment lotions, sun-screen lotions, milks or creams, artificial suntan lotions, creams or creams, shaving creams or foams, aftershave lotions, mascaras or nail varnishes, skin "essences," serums, adhesive or absorbent materials, transdermal patches, and powders can all incorporate one or several UGT inducers and derivatives thereof as well as combinations of these compounds with other additional ingredients.

Cosmetic compositions may also be for orodental use, for example, a toothpaste. In that case, the compositions may contain the usual adjuvants and additives for compositions for oral use and, in particular, surfactants, thickening agents, moisturizing agents, polishing agents such as silica, various active substances such as fluorides, particularly sodium fluoride, and, possibly, sweetening agents such as saccharin sodium.

UGT inducer according to the present invention may be used in cosmetic compositions in accordance with the invention either as individual additions or as a premix in a suitable carrier, and be in the form of solution, dispersion, emulsion, paste, or powder. They may be included individually or as a premix in vehicles such as macro-, micro-, or nanocapsules, liposomes, oleosomes or chylomicrons, macro-, micro-, or nanoparticles or macro-, micro or nanosponges, macro-, micro- or, nanospheres. They may also be adsorbed on organic polymer powders, talcs, bentonites, or other inorganic supports.

Enzyme inducers as well as cosmetic and dermopharmaceutical compositions containing the same, alone or in association, may be used in any form whatsoever, or in a form bound to or incorporated in or absorbed in or adsorbed on macro-, micro-, and nanoparticles, or macro-, micro-, and nanocapsuies, for the treatment of textiles, natural or synthetic fibres, wools, and any materials that may be used for clothing or underwear for day or night intended to come into contact with the skin, such as tights, underclothes, handkerchiefs, or cloths, to exert their cosmetic effect via this skin/textile contact and to permit continuous topical delivery.

The compositions of the present invention can also comprise an orally acceptable carrier if they are to be ingested. Any suitable orally ingestible carrier or carrier form, as known in the art or otherwise, can be used. Non-limiting examples of oral personal care compositions can include, but are not limited to, tablets, pills, capsules, drinks, beverages, powders, vitamins, supplements, health bars, candies, chews, and drops.

The compositions of the present invention can also comprise a liquid that is acceptable for injection in and/or under the skin if the composition is to be injected. Any suitable acceptable liquid as known in the art or otherwise can be used.

The present invention can also be used to manufacture a medicament capable of prophylatically or therapeutically regulating a skin condition including signs of aging, dark rings and stretch marks, hematoma and others. disorders of the blood circulation. This includes delaying, minimizing or preventing visible or tactile discontinuities. Often, but not exclusively, these are part of some longer term therapeutic application, rather than a merely cosmetic or personal care application.

Methods for Improving Skin Condition

The present invention also relates to methods of, among others, protecting, improving the state of the skin, preventing and/or treating imperfections of the skin of a person in need thereof. These cosmetic treatment process is characterized by the fact that one applies, to the skin, hair and/or mucous membranes of the subjects, to protect and/or to improve the state of their skin, prevent and/or treat imperfections of their skin and/or hair and/or mucosa, at least one UGT-inducing agent in a dermatologically acceptable carrier as defined above or a composition containing at least one UGT-inducing agent as defined above. It can be used to treat rings under the eyes and/or hematoma, to protect and/or enhance the state of the skin, to prevent and/or treat imperfections of the skin, to stimulate the body's detoxification, purification and xenobiotic metabolism processes, to increase the detoxification of xenobiotics, to modulate the conversion of androgens and estrogens, to increase muscle mass, to intervene on pigmentation level, to inhibit melanogenesis, to protect the body against pollution, to stimulate the detoxification systems, to stimulate hair and body hair growth, to modulate DHT levels, to intervene on adipocytes and to promote lipolysis The cosmetic treatment process may be implemented, in particular, by applying UGT-inducing agents and the topical or cosmetic or dermopharmaceutical compositions containing them as defined above in accordance with the usual method of use of those compositions. For example: application of creams, gels, sera, lotions, makeup cleansing milks or sunscreen composition to the skin or dried hair, application of a lotion or shampoo to the wet hair, or application of a toothpaste on the gums.

To practice the method, a composition in the form of a skin lotion, cream, gel, foam, ointment, paste, emulsion, spray, conditioner, tonic, cosmetic make-up, lipstick, foundation, nail polish, after-shave or the like, is applied to the skin and intended to stay there (leave-on). The composition can be applied manually, with the aid of spatulas, wipes or similar cosmetic tools. It can also be applied by the use of an occlusive or semi-occlusive patch, an adhesive or non-adhesive tissue Most advantageously, the compositions of the invention are applied to the skin or hair, or mucosa once or twice a day, over an extended period of time, at least one week, preferably one month, even more preferably 3 months, even more preferably for at least about six months, and more preferably still for at least about one year.

Lastly, the present invention covers the use of a composition as defined above as, or for the manufacture of, a cosmetic or dermopharmaceutical composition for the treatment of the skin and symptoms of aging, to protect and/or enhance the state of the skin, to prevent and/or treat imperfections of the skin, to stimulate the body's detoxification, purification and xenobiotic metabolism processes, to increase the detoxification of xenobiotics, to modulate the conversion of androgens and estrogens, to increase muscle mass, to intervene on pigmentation level, to inhibit melanogenesis, to protect the body against pollution, to stimulate the detoxification systems, to stimulate hair and body hair growth, to modulate DHT levels, to intervene on adipocytes and to promote lipolysis.

The present invention concerns the chemical, medical, cosmetic and skin care industries.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

In Vitro Test
Description of the Presence of UGT in FHN and KHN

The cells are cultured in an appropriate medium in the absence (negative control) or in the presence of the test products or product solvent (solvent control). After the 3 days of culture necessary for enzyme induction, the cell layers are rinsed and the total RNA extracted using a commercially-available kit. The total quantity of RNA is determined by spectrophotometry (A260/A280 ratio) and a cDNA bank is created by reverse transcription. Subsequently, the cDNA bank is exposed to specific primers for the gene tested for and real-time PCR(RT-PCR) is implemented. Parameters Ct and Tm are used.

Using that approach, it was possible to demonstrate the presence of mRNA coding for the UGT family in fibroblasts and keratinocytes, more specifically UGT1A1 and UGT1A6 for keratinocytes.

Example 2

In Vitro Test
Induction of UGT activity by Chrysin

Human hepG2 cells were cultured in an appropriate medium (Williams medium) in the presence or absence of the inductor, chrysin, for 3 days At the end of that period, cell lysis was induced, mRNA extracted and RT-PCR conducted Quantification of UGT1A1 mRNA: The study was conducted after 3 days of incubation in the presence of chrysin. The values, shown in Table 1, obtained were normalized on the GADPH internal standard and then expressed as percentages relative to the reference.

|  |  | UGT1A1 | UGT1A1 Induction |
|---|---|---|---|
| Reference |  | 100 |  |
| Chrysin | 3.9 µM | NS | NS |
|  | 7.8 µM | 247 | ×2.5 |
|  | 11.8 µM | 600 | ×6 |

A very marked increase in mRNA was observed in the presence of chrysin with a very clear dose effect.

Example 3

Test In Vitro
Anti-Inflammatory Action of Chrysin

Human keratinocytes and fibroblasts were cultured in an appropriate medium in the presence of various concentrations of chrysin for 24 hours. The cells were then transferred to a product-free medium and exposed to a pro-inflammatory dose of UVB radiation at a dosage of 35 mJ/cm2 for fibroblasts and 30 mJ/cm2 for keratinocytes. Following irradiation, the cells were then post-incubated either in medium alone or in medium containing various concentrations of chrysin vs. a positive control (acetylsalicylic acid) for 24 hours. PGE2 release into the culture medium after 24 hours was determined using an ELISA method.

Table 2 shows the change in PGE2 release post UVB irradiation

|  |  | CHANGE IN PGE2 RELEASE POST-UVB IRRADIATION | |
|---|---|---|---|
|  |  | KERATINOCYTES | FIBROBLASTES |
| acetylsalicylic acid |  | −92% | −95% |
| Chrysin | 2 µM | −75% | −76% |
|  | 3.9 µM | −84% | −85% |
|  | 7.8 µM | −85% | −89% |
|  | 11.8 µM | −86% | −92% |

Significance (all concentrations): $p < 0.01$

Chrysin exerts a marked effect as of the 2 µM concentration. The effect increased up to 85% inhibition of keratinocytic PGE2, but without a dose effect. With fibroblasts, the efficacy regularly increased, reaching 92% at the highest concentration (11,8 µM). Acetylsalicylic acid was an excellent anti-inflammatory inducing almost total inhibition of PGE2, greater than 90% for both cell types.

Example 4

In Vivo Study
56-Day Clinical Trial Versus Placebo

The efficacy study of, was conducted in a group of female volunteers (average age 32.7) presenting with violet rings but no bags under their eyes. The method used was image analysis, conducted on photographs taken under standardized conditions. The photographs were taken with a digital camera. The analysis of image color was conducted using an image processing program, which determined the parameters R (red), G (green) and B (blue). These parameters were converted to L, a* and b* parameters, using an analysis program.

The volunteers applied a mild cream-gel to each half of the face. A placebo cream-gel was applied to the left side and 2% HALOXYL™ (see example 5) to the right side. Applications were conducted twice daily for 56 days. Each subject acted as her own control.

Each subject's ring was characterized by the differential of parameters ΔL, Δa* and Δb*, shown in Table 3, between zone vs. ring-free zone, at the outer angle of the eye. An anti-ring product should increase parameters ΔL and Δb* and decrease Δa*.

|  | Half-face HALOXYL ® (2%) | | | Half-face PLACEBO | | |
|---|---|---|---|---|---|---|
|  | ΔL | Δa* | Δb* | ΔL | Δa* | Δb* |
| Mean (n = 22) | −1% | −1.,5% | +10% | −2.4% | −2.8% | +2.6% |
| Significance vs. T0 | NS | p < 0.05 | p < 0.01 | NS | NS | NS |
| Significance treated vs. placebo | ΔL NS | | Δa* p < 0.05 | | Δb* p < 0.01 | |

A significant difference, shown in Table 4, was obtained for the improvement in parameters Δa* and Δb* on the treated side with −12.5% and +10% of mean change, in the expected direction, i.e. a decrease in Δa* and an increase in Δb* (the treated side rings lost their violet component). ΔL showed very little variation and the changes were not significant for either side.

|  | Δa* | Δb* |
|---|---|---|
| Mean (n = 22) | −12.5% | +10% |
| Significance | P < 0.05 | P < 0.01 |
| Nr of responders | 16/22 | 14/22 |
| Mean responder's response | −19.5% Decrease in the red component | +19% Decrease in the blue component |

For the responders (Subjects responding positively to treatment), the improvement in the red and blue components of their rings was significant, vs. D0. with a mean difference of 19%. Overall, the violet (red+blue) appearance was significantly alleviated. This was the expected effect required of a product treating or reducing the appearance of rings.

Example 5

Anti-Wrinkles Cream-Gel

| Ingredients | INCI | | % by wt. |
|---|---|---|---|
| Phase A | | | |
| Water Deionised | Water (Aqua) | | qs 100% |
| Carbopol Ultrez 10 | Carbomer | Noveon | 0.30 |
| Glycerin | Glycerin | | 5.00 |
| Phase B | | | |
| Natrosol 250M | Hydroxyethylcellulose | | 0.30 |
| Pemulen TR2 | C10-30 Alkyl Acrylate Crosspolymer | Noveon | 0.20 |
| Crodamol CAP | Cetearyl Octanoate | Croda | 6.00 |
| Crillet 1 | Polysorbate 20 | Croda | 0.10 |
| Phase C | | | |
| NaOH 30% | Sodium Hydroxide | | 0.46 |
| Potassium sorbate | Potassium Sorbate | | 0.10 |
| Preservative | | | qs |
| Phase D | | | |
| HALOXYL ® | Aqua (Water) (and) Glycerin (and) Steareth-20 (and) Chrysin (and) N-Hydroxysuccinimide (and) Palmitoyl Oligopeptide (and) Palmitoyl Tetrapeptide-3 | Sederma | 2.00 |

Example 6

Anti-Aging Night Cream

| Ingredients | INCI | | % by wt. |
|---|---|---|---|
| Phase A | | | |
| Water deionised | Water (Aqua) | | qs 100% |
| Ultrez 10 | Carbomer | Noveon | 0.10 |
| Phase B | | | |
| Glycerin | | | 5.00 |
| Phase C | | | |
| Volpo S2 | Steareth 2 | Croda | 0.60 |
| Crodafos CES | Cetearyl Alcohol (and) Dicetyl Phosphate (and) Ceteth 10 Phosphate | Croda | 4.00 |
| Crodamol STS | PP3 Benzyl Ether Myristate | Croda | 4.00 |
| Crodamol OSU | Dioctyl Succinate | Croda | 5.00 |
| Crill 3 | Sorbitan Stearate | Croda | 1.60 |
| Methyl Parabens | Methyl Parabens | | 0.30 |
| Phase D | | | |
| Potassium Sorbate | Potassium Sorbate | | 0.10 |
| Phase E | | | |
| NaOH 30% | Sodium Hydroxide | | 0.30 |
| Water deionised | Water (Aqua) | | 3.00 |
| Phase F | | | |
| Matrixyl ® 3000 | Glycerin (and) Water (Aqua) (and) Butylene Glycol (and) Carbomer (and) Polysorbate 20 (and) Palmitoyl Oligopeptide(and) Palmitoyl Tetrapeptide-3 | Sederma | 3.00 |
| chrysin | | | 0.01 |
| Phase G | | | |
| Fragrancee | Fragrance | | 0.10 |

The emulsion is prepared as follows: phase A: disperse Ultrez 10 in water and allow to swell for 20 minutes. Add phase B. Heat to 75° C. Heat phase C separately at 75° C. Mix the two phases while stirring and blend. Add phase D. Neutralize with phase E. Cool to 30° C. Add phases F and G. Adjust the pH to ~6 with NaOH.

The cream is suitable for fragile, elderly skins to correct crow's feet, wrinkles and dryness and reduce erythema and irritation.

Example 7

Anti-Hair Loss Tonic

| Ingredients | INCI | | % by wt. |
|---|---|---|---|
| Phase A | | | |
| Incroquat Behenyl TMC | Behentrionium Chloride (and) Cetearyl Alcohol | Croda | 3.00 |
| Phenyl Trimethicone | | | 1.00 |
| Preservative | | | 0.20 |
| Phase B | | | |
| Potassium Sorbate | Potassium Sorbate | | 0.10 |
| Water deionised | Water (Aqua) | | qs 100% |
| Phase C | | | |
| Apigenin | Apigenin | | 0.0001 |
| PROCAPIL ® | Butylene Glycol (and) Water (Aqua) (and) PPG-26-Buteth-26 (and) PEG-40 Hydrogenated castor Oil (and) Apigenin (and) Oleanolic Acid (and) Biotinyl Tripeptide-1 | Sederma | 3.00 |
| Phase D | | | |
| Fragrance | Fragrance | | 0.10 |
| Phase E | | | |
| Water deionised | Water (Aqua) | | 0.25 |
| Sarcolactic Acid | | | 0.025 |

The lotion is prepared as follows: heat phase A to 85° C. Heat phase B to 85° C. Run phase A into phase B while stirring. Blend. Cool to 35° C. Add phase C and phase D. Adjust the pH to ~5.5 with phase E.

The lotion promotes the anchoring of telogen hairs in the dermis through regeneration of the epithelial sheath. The lotion slows hair loss, promotes fresh growth and enhances the state of 'health' of the hair follicles.

Example 8

After-Shave Balm

| Ingredients | INCI | | % by wt. |
|---|---|---|---|
| Phase A | | | |
| Water deionised | Water (Aqua) | | qs 100% |
| Ultrez 10 | Carbomer | Noveon | 0.20 |
| Phase B | | | |
| Glycerin | | | 5.00 |
| Mixed Parabens | | | 0.20 |
| Phase C | | | |
| Crodamol IPP | Isopropyl Palmitate | Croda | 4.00 |
| Cithrol GMS | Glyceryl Stearate(and) PEG-100 Stearate | Croda | 1.00 |
| Phase D | | | |
| Pemulen TR2 | Acrylates/C10-30 Alkyl Acrylate Crosspolymer | Noveon | 0.20 |
| DC 200 | Dimethicone | Dow Corning | 2.00 |
| Phase E | | | |
| Potassium Sorbate | Potassium Sorbate | | 0.10 |
| Phase F | | | |
| NaOH 38% | Sodium Hydroxide | | 0.40 |
| Water deionised | Water (Aqua) | | 4.00 |
| Phase G | | | |
| Luteolin | | | 0.0001 |
| BIRCH SAP | Betula Alba Sap (and) Glycerin | Sederma | 3.00 |
| Phase H | | | |
| Fragrance | Fragrance | | 0.10 |

The balm is prepared as follows. Phase A: disperse Ultrez 10 in water and allow to swell for 20 minutes. Mix phase B and heat to 60° C. until dissolved. Add phase B to phase A under stirring. Heat phase (A+B). Weigh phase C and heat to 75° C. Add phase C to phase (A+B) under stirring. Thoroughly blend. Add phase D. Add phase E at about 50° C. Neutralize with phase F. Add phases G and H at approximately 35° C. and at pH ~6.30. This pleasant, easy-to-apply balm procures an immediate and lasting moisturizing effect with a sensation of wellbeing. It decreases razor burn and tenseness and imparts protection.

Example 9

Anti Rings Anti Puffy Eyes Gel

| Ingredients | INCI | | % by wt. |
|---|---|---|---|
| Part A | | | |
| Water deionised | Water (Aqua) | | qs 100% |
| Ultrez 10 | Carbomer | Noveon | 0.20 |
| Part B | | | |
| Glycerin | | | 5.00 |
| Preservative | | | qs |
| Part C | | | |
| Hydroxyethylcellulose | | | 0.20 |
| Part D | | | |
| Pemulen TR2 | Acrylates/C10-30 Alkyl Acrylate Crosspolymer | Noveon | 0.20 |
| Crodamol CAP | Cetearyl Ethylhexanoate | Croda | 6.00 |
| Part E | | | |
| Potassium Sorbate | Potassium Sorbate | | 0.10 |
| Part F | | | |
| Water deionised | Water (Aqua) | | 4.00 |
| NaOH 30% | Sodium Hydroxide | | 0.46 |
| Part G | | | |
| Quercetin | | | 0.0005 |
| Déféroxamine | | | 0.015 |
| EYELISS ® | Water (and) Glycerin (an) Hesperidin Methyl Chalcone (and) Steareth-20 (and) Dipeptide-2 (and) Palmitoyl Tetrapeptide-3 | Sederma | 3.00 |
| Crillet 1 | Polysorbate 20 | Croda | 0.50 |
| Part H | | | |
| Fragrance | Fragrance | | qs |

The gel is prepared as follows. Phase A: disperse Ultrez 10 in water and allow to swell for 15 minutes. Phase B: heat glycerin to 60° C. Dissolve the preservatives. Cool to 40° C. Add phase C to phase B and blend. Add phase (B+C) to phase A under impeller stirring. Allow to swell for 1 hour. Add phase D, then phase E to phase (A+B+C). Blend. Neutralize with phase F. Allow to swell for 1 hour. Incorporate phase G and blend. Then add phase H.

Twice daily application of this gel around the eyes procures a decrease in the bags under the eyes, a decongestive effect and alleviation of rings under the eyes.

Example 10

Protective Hair Spray

| Ingredients | INCI | | % by wt. |
|---|---|---|---|
| Part A | | | |
| Water deionised | Water (Aqua) | | qs 100% |
| Ethanol | | | 10.00 |
| Crillet 1 | Polysorbate 20 | Croda | 0.40 |
| Incroquat CTC 30 | Cetrimonium Chloride | Croda | 1.00 |
| Part B | | | |
| Diosmetin | | | 0.001 |
| HELIOGENOL ™ | Butylene Glycol (and) *Helianthus Annuus* (Sunflower) Seed Extract | Sederma | 5.00 |
| Preservative | | | qs |
| Part C | | | |
| Water deionised | Water (Aqua) | | 0.50 |
| NaOH | Sodium Hydroxide | | 0.05 |

The spray is prepared as follows: mix phase A. Add phase B. Adjust the pH to ~5-5.5 with phase C.

The hair spray protects and repairs the external sheath of the hair. It neutralizes UV light-induced oxidizing free radicals and detoxifies the hair and scalp from environmental aggressions.

Example 11

Anti-Wrinkle Cream with Skin Whitening Activity

| Ingredients | INCI | | % by wt. |
|---|---|---|---|
| Phase A | | | |
| Water deionised | Water (Aqua) | | qs 100% |
| Ultrez 10 | Carbomer | Noveon | 0.10 |
| Phase B | | | |
| Transcutol | | | 3.00 |
| Glycerin | | Croda | 8.00 |
| Phase C | | | |
| Potassium Sorbate | Potassium Sorbate | | 0.10 |
| Phase D | | | |
| Volpo S2 | Steareth 2 | Croda | 0.60 |
| Crodafos CES | Cetearyl Alcohol (and) Dicetyl Phosphate (and) Ceteth 10 Phosphate | Croda | 4.00 |
| DC 344 | Cyclomethicone | Dow Corning | 2.00 |
| Crodamol GTCC | Caprylic/Capric Triglyceride | Croda | 10.00 |
| Crill 3 | Sorbitan Stearate | Croda | 1.60 |
| Mixed Parabens | | | 0.30 |
| Phase E | | | |
| NaOH 30% | Sodium Hydroxide | | 0.30 |
| Water deionised | Water (Aqua) | | 3.00 |
| Phase F | | | |
| Kaempferol | | | 0.00008 |
| Matrixyl ® 3000 | Glycerin (and) Butylene Glycol (and) Aqua (Water) (and) Carbomer (and) Polysorbate-20 (and) Palmitoyl Oligopeptide (and) Palmitoyl Tetrapeptide-3 | Sederma | 3.00 |
| LUMISKIN ® | Caprylic/Capric Triglyceride (and) Diacetyl Boldine | Sederma | 4.00 |
| Fragrance | Fragrance | | 0.10 |

The emulsion is prepared as follows. Phase A: disperse Ultrez 10 in water and allow to swell for 20 minutes. Then add phase B and phase C. Heat to 75° C. Heat phase D separately to 75° C. Mix thoroughly. Run phase D into phase (A+B+C) under stirring. Blend, then neutralized with phase E. Cool to 35° C. Add phase F. The cream is suitable for the cosmetic treatment of elderly skin, inducing the disappearance of crow's feet, wrinkles and hyperpigmentation spots and stimulating the detoxification systems.

Example 12

Anti-Stretch Mark Slimming Cream

| Ingredients | INCI | | % by wt. |
|---|---|---|---|
| Phase A | | | |
| Water deionised | Water (Aqua) | | qs 100% |
| Ultrez 10 | Carbomer | Noveon | 0.40 |
| Phase B | | | |
| Glycerin | | | 5.00 |
| Phenova | Phenoxyethanol (and) Mixed Parabens | Crodarom | 0.80 |
| Phase C | | | |
| Crodamol OP | Ethylhexyl Palmitate | Croda | 4.00 |
| Crodacol CS90 | Cetearyl alcohol | Croda | 0.50 |
| Crodamol ML | Myristyl Lactate | Croda | 0.30 |
| Crillet 1 | Polysorbate 20 | Croda | 1.00 |
| Phase D | | | |
| Pemulen TR2 | Acrylates/C10-30 Alkyl Acrylate Crosspolymer | Noveon | 0.20 |
| DC 345 | Cyclomethicone | Dow Corning | 2.00 |
| Phase E | | | |
| Potassium Sorbate | Potassium Sorbate | | 0.10 |
| Phase F | | | |
| NaOH 38% | Sodium Hydroxide | | 0.60 |
| Water deionised | Water (Aqua) | | 6.00 |
| Phase G | | | |
| Galangin | | | 0.0003 |
| UNISLIM ® | Ilex Paraguariensis (Leaf) Extract - Aqua (Water) - Butylene Glycol - Coffea Arabica (Coffee Seed) Bean Extract - PEG-60 Almond Glycerides - Glycerin - Cetyl Hydroxyethylcellulose | Sederma | 3.00 |
| MATRIXYL ® 3000 | Glycerin (and) Butylene Glycol (and) Aqua (Water) (and) Carbomer (and) Polysorbate-20 (and) Palmitoyl Oligopeptide (and) Palmitoyl Tetrapeptide-3 | Sederma | 3.00 |
| DARUTOSIDE | Siegesbeckia Orientalis Extract | Sederma | 3.00 |

The emulsion is prepared as follows. Phase A: disperse Ultrez 10 in water and allow to swell for 20 minutes. Mix phase B and heat to 60° C. until completely dissolved. Add phase B to phase A under stirring. Heat phase (A+B). Weigh phase C and heat to 75° C. Add phase C to phase (A+B) under stirring. Carefully blend. Add phase D. Add phase E at about 50° C. Neutralized with phase F. Add phases G and H at about 35° C., pH ~6.30.

Example 13

Anti-Stretch Mark Gel

| Ingredients | INCI | | % by wt. |
|---|---|---|---|
| Phase A | | | |
| Water deionised | Water (Aqua) | | qs 100% |
| Phase B | | | |
| Butylene glycol | | | 5.00 |
| Phenova | Phenoxyethanol (and) Mixed Parabens | Crodarom | 0.80 |
| Phase C | | | |
| Crill 3 | Sorbitan Stearate | Croda | 1.20 |
| Crillet 3 | Polysorbate 60 | Croda | 3.00 |
| DC 200 | Dimethicone | Dow Corning | 2.00 |
| Crodamol IPM | Isopropyl Myristate | Croda | 5.00 |
| Crodamol W | Stearyl Heptanoate | Croda | 0.30 |

| Ingredients | INCI | | % by wt. |
|---|---|---|---|
| Crodamol GTCC | Caprylic/Capric Triglyceride | Croda | 5.00 |
| Crodacol CS90 | Cetearyl Alcohol | Croda | 2.00 |
| Phase D | | | |
| Carbopol 980 at 2% | Carbomer | BF Goodrich | 10.00 |
| DC 345 | Cyclomethicone | | 2.00 |
| Phase E | | | |
| Potassium Sorbate | Potassium Sorbate | | 0.10 |
| Phase F | | | |
| NaOH 38% | Sodium Hydroxide | | 0.20 |
| Water deionised | Water (Aqua) | | 2.00 |
| Phase G | | | |
| Water deionised | Water (Aqua) | | 10.00 |
| Pal-Gly-His-Lys | | Sederma | 0.0003 |
| Pal-Gly-Gln-Pro-Arg (SEQ ID NO: 1) | | Sederma | 0.00015 |
| Rutine | | Sederma | 0.10 |
| Bowman Birk Inhibitor | Siegesbeckia Orientalis Extract | Sederma | 0.0001 |

The gel is prepared as follows. Blend phase B and run into phase A. Disperse Ultrez 10 in water and allow to swell for 20 minutes. Mix phase B and heat at 60° C. until dissolved. Add phase B to phase A under stirring. Heat phase (A+B). Weigh phase C and heat to 75° C. Add phase C to phase (A+B) under stirring. Blend thoroughly, then add phase D. Add phase E at about 50° C. Neutralize with phase F. Add phases G and H at about 35° C.

Rutin and Bowman Birk Inhibitor contribute to the anti-stretch mark activity by stimulating tissue regeneration, inhibiting protein cleavage and strengthening the binding of collagen fibers.

Example 14

Moisturizing Face Gel

| Ingredients | INCI | | % by wt. |
|---|---|---|---|
| Phase A | | | |
| Water deionised | Water (Aqua) | | qs 100% |
| Ultrez 10 | Carbomer | Noveon | 0.20 |
| Phase B | | | |
| Glycerin | | | 3.00 |
| Phenova | Phenoxyethanol (and) Mixed Parabens | Crodarom | 0.80 |
| Phase C | | | |
| Crillet 1 | Polysorbate 20 | Croda | 0.50 |
| Phase D | | | |
| Potassium Sorbate | Potassium Sorbate | | 0.10 |
| Phase E | | | |
| Pemulen TR1 | Acrylates/C10-30 Alkyl Acrylate Crosspolymer | Noveon | 0.20 |
| DC 345 | Cyclomethicone | Dow Corning | 3.00 |
| Phase F | | | |
| NaOH 38% | Sodium Hydroxide | | 0.40 |
| Water deionised | Water (Aqua) | | 4.00 |

| Ingredients | INCI | | % by wt. |
|---|---|---|---|
| Phase G | | | |
| Naringenin | | | 0.02 |
| MOIST-24 ® | Imperata Cylindrica (root) Extract (and) water (and) Glycerin (and) PEG-8 (and) Carbomer | Sederma | 5.00 |

The emulsion is prepared as follows. Phase A: disperse Ultrez 10 in water and allow to swell for 20 minutes. Mix phase B and heat at 60° C. until dissolved. Add phase B to phase A under stirring. Heat phase (A+B). Weigh phase C and heat to 75° C. Add phase C to phase (A+B) under stirring. Carefully blend and add phase D. Add phase E at about 50° C. Neutralized with phase F. Add phase G at about 35° C.

MOIST-24® is a moisturizing plant extract marketed by SEDERMA (WO 01/62218 dated Aug. 30, 2001).

Example 15

Soothing Day Cream

| Ingredients | INCI | | % by wt. |
|---|---|---|---|
| Phase A | | | |
| Water deionised | Water (Aqua) | | qs 100% |
| Ultrez 10 | Carbomer | Noveon | 0.20 |
| Phase B | | | |
| Potassium Sorbate | Potassium Sorbate | | 0.10 |
| Phase C | | | |
| Butylene glycol | | | 2.00 |
| Phenova | Phenoxyethanol (and) Mixed Parabens | Crodarom | 0.80 |
| Phase D | | | |
| Crill 3 | Sorbitan Stearate | Croda | 1.00 |
| Crillet 3 | Polysorbate 60 | Croda | 2.50 |
| DC 200 | Dimethicone | Dow Corning | 2.50 |
| Crodamol TN | Isotridecyl Isononanoate | Croda | 5.00 |
| Crodamol GTCC | Caprylic/Capric Triglyceride | Croda | 5.00 |
| Crodamol SS | Cetyl Ester | Croda | 1.00 |
| Super Hartolan | Lanolin Alcohol | Croda | 0.50 |
| Super Sterol Ester | C10-C30 Cholesterol/Lanosterol ester | Croda | 0.30 |
| Crodacol CS90 | Cetearyl Alcohol | Croda | 3.00 |
| Phase E | | | |
| NaOH 30% | Sodium Hydroxide | | 0.25 |
| Water deionised | Water (Aqua) | | 2.50 |
| Phase F | | | |
| Passion Flower Extract | | | 5.00 |
| CALMOSENSINE ® | Butylene Glycol (and) water (and) Laureth-3 (and) Hydroxyethylcellulose (and) Acetyl-Dipeptide-1-cetylester | Sederma | 4.00 |
| Fragrance | Fragrance | | 0.10 |

The emulsion is prepared as follows. Phase A: disperse Ultrez 10 in water and allow to swell for 20 minutes. Add phase B and phase C. Heat to 75° C. Heat phase D separately to 75° C. and mix well. Run phase D into phase (A+B+C)

under stirring. Blend, then neutralize with phase E. Cool to 35° C. Add phase F. Calmosensine® is an analgesic peptide marketed by SEDERMA (WO 98/07744 dated Feb. 26, 1998).

Example 16

Cream for Mature Skin

| Ingredients | INCI | | % by wt. |
|---|---|---|---|
| Phase A | | | |
| Water deionised | Water (Aqua) | | qs 100% |
| Ultrez 10 | Carbomer | Noveon | 0.20 |
| Phase B | | | |
| Glycerin | | Croda | 3.50 |
| Phase C | | | |
| Potassium Sorbate | Potassium Sorbate | | 0.10 |
| Phase D | | | |
| Volpo S10 | Steareth 10 | Croda | 1.50 |
| Crodafos CES | Cetearyl Alcohol (and) Dicetyl Phosphate (and) Ceteth 10 Phosphate | Croda | 3.50 |
| DC 200 | dimethicone | Dow Corning | 2.00 |
| Crodamol OSU | Diethylhexyl Succinate | Croda | 7.00 |
| Crill 3 | Sorbitan Stearate | Croda | 0.40 |
| Mixed Parabens | | | 0.30 |
| Phase E | | | |
| NaOH 30% | Sodium Hydroxide | | 0.20 |
| Water deionised | Water (Aqua) | | 4.00 |
| Phase F | | | |
| Genistein | | | 0.0002 |
| DERMAXYL ® | C12-15 Alkyl benzoate (and) Tribehenin (and) Ceramide 2 (and)PEG-10 Rapeseed Sterol (and) Palmitoyl Oligopeptide | Sederma | 3.00 |
| STEROCARE ® | *Trifolium Pratense* (Clover) Flower Extract (and) Glycerin (and) Butylene Glycol (and) Lecithin | Sederma | 3.00 |
| Fragrance | Fragrance | | 0.10 |

The emulsion is prepared as follows. Phase A: disperse Ultrez 10 in water and allow to swell for 20 minutes. Add phase B and phase C. Heat to 75° C. Heat phase D separately at 75° C. Mix thoroughly. Run phase D into phase (A+B+C) under stirring. Blend, then neutralize with phase E. Cool to 35° C. Add phase F. Sterocare® is marketed by SEDERMA as an active substance for mature skins (FR 2 769 502 dated Apr. 14, 2000. WO 99/18927 dated Apr. 22, 1999).

Example 17

Anti Rings under Eyes Lotion

| Ingredients | INCI | | % by wt. |
|---|---|---|---|
| Phase A | | | |
| Water deionised | Water (Aqua) | | qs 100% |
| Ultrez 10 | Carbomer | Noveon | 0.20 |
| Phase B | | | |
| Glycerin | | Croda | 3.00 |
| Phase C | | | |
| Potassium Sorbate | Potassium Sorbate | | 0.10 |
| Phase D | | | |
| Volpo S10 | Steareth 10 | Croda | 1.50 |
| Crodafos CES | Cetearyl Alcohol (and) Dicetyl Phosphate (and) Ceteth 10 Phosphate | Croda | 3.00 |
| DC 200 | dimethicone | Dow Corning | 2.00 |
| Crodamol OSU | Diethylhexyl Succinate | Croda | 5.00 |
| Crill 3 | Sorbitan Stearate | Croda | 0.40 |
| Mixed Parabens | | | 0.30 |
| Phase E | | | |
| NaOH 30% | Sodium Hydroxide | | 0.20 |
| Water deionised | Water (Aqua) | | 4.00 |
| Phase F | | | |
| MATRIXYL ® 3000 | Glycerin (and) Butylene Glycol (and) Aqua (Water) (and) Carbomer (and) Polysorbate-20 (and) Palmitoyl Oligopeptide (and) Palmitoyl Tetrapeptide-3 | Sederma | 2.00 |
| Lactoferrine | | | 0.10 |
| Yin Chin extract | | | 5.00 |

The emulsion is prepared as follows. Phase A: disperse Ultrez 10 in water and allow to swell for 20 minutes. Add phase B and phase C. Heat to 75° C. Heat phase D separately to 75° C. Mix thoroughly. Run phase D into phase (A+B+C) under stirring. Blend, then neutralized with phase E. Cool to 35° C. Add phase F.

Example 18

Moisturizing and Anti-Wrinkle Foundation

| Ingredients | INCI | | % by wt. |
|---|---|---|---|
| Phase A | | | |
| Water deionised | Water (Aqua) | | qs 100% |
| KOH 10% | Potassium hydroxide | | 1.30 |
| Crillet 4 NF | Polysorbate 80 | Croda | 0.10 |
| Phase B | | | |
| Titanium dioxide | | | 6.00 |
| Talc | | | 3.05 |
| Yellow iron oxide | | | 1.80 |
| Red iron oxide | | | 1.00 |
| Black iron oxide | | | 0.15 |
| Phase C | | | |
| Propylene glycol | | | 4.00 |
| Veegum Regular | Magnesium Aluminum Silicate | | 1.00 |

-continued

| Ingredients | INCI | | % by wt. |
|---|---|---|---|
| Phase D | | | |
| Propylene glycol | | | 2.00 |
| Cellulose gum | Sodium Carboxymethylcellulose | | 0.12 |
| Phase E | | | |
| Cromollient DP3-A | Di-PPG-3 Myristyl Ether Adipate | Croda | 12.00 |
| Crodamol ISNP | Isostearyl Neopentanoate | Croda | 4.00 |
| Crodafos CS 20 | Cetearyl Alcohol (and) Ceteth-20 Phosphate (and) Dicetyl Phosphate | Croda | 3.00 |
| Volpo S-10 | Steareth-10 | Croda | 2.00 |
| Crodacol C-70 | Cetyl alcohol | Croda | 0.62 |
| Volpo S-2 | Steareth-2 | Croda | 0.50 |
| DERMAXYL ® | C12-15 Alkyl benzoate (and) Tribehenin (and) Ceramide 2 (and)PEG-10 Rapeseed Sterol (and) Palmitoyl Oligopeptide | Sederma | 3.00 |
| Phytic Acid | | | 0.08 |
| Chrysin | | | 0.005 |
| Phase F | | | |
| Germaben II | Propylene glycol (and) Diazolidinyl Urea (and) Methylparaben (and) Propylparaben | | 1.00 |

The emulsion is prepared as follows. Phase A: disperse Ultrez 10 in water and allow to swell for 20 minutes. Premix the pigments. Add phase B to phase A until the pigments are dispersed. Begin heating. Heat phase C separately and mix thoroughly. Run phase C into phase (A+B) under stirring. Prepare phase D separately, mixing thoroughly. Run phase D into phase (A+B+C) under stirring. Blend. Prepare phase E separately and mix thoroughly. Run phase E into phase (A+B+C+D) under stirring. Adjust the pH to 7.5 and blend.

Example 19

Protective Balm for the Lips

| Ingredients | INCI | | % by wt. |
|---|---|---|---|
| Phase A | | | |
| Ricin Oil | Castor (Ricinum communis) Oil | | 5.00 |
| Crodamol PTIS | Pentaerythrityl Tetraisostearate | Croda | qs 100% |
| Syncrowax HRC | Tribehenin | Croda | 6.00 |
| Syncrowax ERLC | C18-36 Acid Glycol Ester | Croda | 6.00 |
| Novol | Oleoyl Alcohol | Croda | 9.00 |
| Crodacol C90 | Cetyl Alcohol | Croda | 4.00 |
| Super Sterol Ester | C10-30 Cholesterol/Lanosterol Esters | Croda | 2.00 |
| Carnauba Wax | Carnauba (Copernicia cerifera) wax | | 5.00 |
| Paraffin | Paraffin | | 4.00 |
| Phase B | | | |
| MAXI-LIP | Octyl Palmitate-Tribehenin-Sorbitan Isostearate-Palmitoyl-Oligopeptide | Sederma | 1.00 |
| Chrysin | | | 0.004 |
| Mixed Parabens | | | qs |
| Phase C | | | |
| Crill 6 | Sorbitan Isostearate | | 7.00 |
| Polyolprepolymer 14 | PPG-51/SMDI Copolymer | | 5.00 |
| Fragrance | | | qs |

The balm is prepared as follows. Phase A: melt the ingredients at 80° C. Blend. Incorporate phase B, then phase C. Blend and mold.

---

The invention claimed is:

1. A cosmetic or dermopharmaceutical composition comprising:
   a) at least one UGT inducer compound, said UGT inducer compound being present at a concentration from about 0.000001% (w/w) to about 10% (w/w);
   b) a chelating agent being N-hydroxysuccinimide, present in an amount from about 0.00001% (w/w) to about 10% (w/w);
   c) at least one peptide, said peptide being present in an amount from about 0.000001% (w/w) to about 10% (w/w); and
   d) a cosmetically acceptable carrier suitable for topical application.

2. The cosmetic or dermopharmaceutical composition of claim 1 wherein said UGT inducer compound is a flavonoid compound selected from the group consisting of chrysin, techtochrysin, chrysin 5-methylether, galangin, galangin 5-methylether, pinocembrin, pinobanksin, apigenin, fisetin, hesperitin, kaempferol, morin, myrecetin, naringenin, quercetin, quercitin, rutin, myricetin, rhamnetin, luteolin, naringin, hesperidin, naringenin, hesperitin, phloridzin, diosmin, fisetin, vitexin, neohesperidin dihydrochalcone, glucosyl rutin, genistein, alpha-glucosylrutin, alpha-glucosylmyrictrin, alpha-glucosylisoquercitrinitrin, alpha-glucosylquercitrin, troxerutin, monoxerutin, phlorizin, robinetin, gossypetin, taxifolin, eriodictyol, troxerutin, tangeretin, catechin, epicatechin, gallocatechin, epigallocatechin, epigallocatechin gallate, epicatechin gallate, toringin, primetin, cosmosiin, apiin, galuteolin, glucoluteolin, acacetin, linarin, diosmetin, baicalein, trifolin, astragalin, roninin, kaempferitrin, isoquercitrin-datiscetin, quercetagitin, quercetagitrin, rhamnetin, isorhamnetin, wogonin, scutellarein, cyanidin, delphinidin, pelargonidin, calycopterin, isovitexin, alpha-gisoquercitrintin, alpha-mannosylrutin, nepetin, tangeretin, tricetin, tricin, pinocembrin, biochaninA, daidzein, puerarin, umbelliferone, esculin, esculoside, esculetin scopoletin, berberin, dimers: amentoflavone, ginkgetin, isoginkgetin, pharmaceutical derivatives: androstanediol, bilirubin, codeine, ethynylestradiol, furosemide, gemfibrozil, hydromorphone, hyodeoxycholic acid, imipramine, ketoprofen, morphine, naloxone, 1-naphthol, naproxene, propofol, valproic acid and derivatives, zidovudine, lamotrigine and gamma-orizanol.

3. The cosmetic or dermopharmaceutical composition of claim 1 wherein said UGT inducer compound is chrysin, or an analog, stereoisomer, glycoside or derivative thereof.

4. The cosmetic or dermopharmaceutical composition of claim 2 wherein said flavonoid compound is a plant extract.

5. The cosmetic or dermopharmaceutical composition of claim 1 wherein said UGT inducer compound is present at a concentration from about 0.00001% (w/w) to about 1% (w/w).

6. The cosmetic or dermopharmaceutical composition of claim 1 wherein said composition is in the form of an aqueous or dilute alcoholic solution, a water in oil emulsion, an oil in water emulsion, a microemulsion, an aqueous gel, an anhydrous gel, a serum or a vesicle dispersion.

7. The cosmetic or dermopharmaceutical composition of claim 1 further comprising at least one additional ingredient selected from the group consisting of healing agents, anti-aging agents, anti-wrinkle agents, soothing agents, moisturizers, antibacterial agents, pesticides, antifongic agents, anti-inflammatory drugs, anti-pruriginous agents, anaesthetics, antiviral agents, keratolytic agents, free radicals scavengers, antiseborrheics, antidandruff agents, anti-acne agents, agents modulating differentiation, proliferation or pigmentation of skin, penetration accelerating agents, cleaning agents, hair conditioning agents, skin conditioning agents, hair styling agents, hair growth promoters, fragrances, sunscreen and/or sunblock compounds, pigments, film formers, hair colors, make-up agents, detergents, pharmaceutical drugs, thickening agents, emulsifiers, humectants, emollients, antiseptic agents, deodorant actives, dermatologically acceptable carriers, surfactants, abrasives, absorbents, aesthetic components, fragrances, colorings/colorants, essential oils, skin sensates, astringents, anti-caking agents, antifoaming agents, antimicrobial agents, antioxidants, binders, biological additives, enzymes, enzymatic inhibitors, enzyme-inducing agents, coenzymes, plant extracts, ceramides, peptides, buffering agents, bulking agents, chelating agents, chemical additives, colorants, cosmetic astringents, cosmetic biocides, denaturants, drug astringents, external analgesics, quaternary derivatives, substantivity increasing agents, opacifying agents, pH adjusters, propellants, reducing agents, sequestrants, skin bleaching and lightening agents, aloe vera, pantothenic acid and its derivatives, allantoin, bisabolol, dipotassium glycyrrhizinate, skin treating agents, thickeners, vitamins and derivatives thereof, and lignans.

8. The cosmetic or dermopharmaceutical composition of claim 1 or claim 7 wherein said composition further comprises an optional ingredient selected from the group consisting of sugar amines, glucosamine, D-glucosamine, N-acetyl glucosamine, N-acetyl-D-glucosamine, mannosamine, N-acetyl mannosamine, galactosamine, N-acetyl galactosamine, vitamin B3 and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, bisabolol, salicylic acid compounds, peptides and their derivatives, di-, tri-, tetra-, penta-, and hexapeptides and their derivatives, lys-thr-thr-lys-ser (SEQ ID NO:2), palmitoyl-lys-thr-thr-lys-ser (SEQ ID NO:3), carnosine, N-acyl amino acid compounds, retinoids, retinyl propionate, retinol, retinyl palmitate, retinyl acetate, retinal, retinoic acid, water-soluble vitamins, ascorbates, vitamin C, ascorbic acid, ascorbyl glucoside, ascorbyl palmitate, magnesium ascorbyl phosphate, sodium ascorbyl phosphate, vitamins and their salts and derivatives, provitamins and their salts and derivatives, water soluble vitamins, vitamin B, vitamin B derivatives, vitamin B1, vitamin B2, vitamin B6, vitamin B12, vitamin K, vitamin K derivatives, pantothenic acid, pantothenyl ethyl ether, panthenol, biotin, amino acids and their salts and derivatives, N-acyl amino acid compounds, water soluble amino acids, asparagine, alanine, indole, glutamic acid, water insoluble vitamins, vitamin A, vitamin D, vitamin E, vitamin F, water insoluble amino acids, tyrosine, tryptamine, particulate materials, sunscreen actives, anti-cellulite agents, anti-acne agents, keratolytic agents, butylated hydroxytoluene, butylated hydroxyanisole, allantoin, tocopherol nicotinate, tocopherol, tocopherol esters, palmitoyl-gly-his-lys, phytosterol, dexpanthenol, panthenol, anti-wrinkle agents, anti-atrophy agents, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, particulate materials, pigment materials, natural colors, antimicrobial agents, cosmetic biocides, antidandruff agents, piroctone olamine, 3,4,4'- trichlorocarbanilide, triclocarban, zinc pyrithione, hydroquinone, kojic acid, ascorbic acid, magnesiuim ascorbyl phosphate, ascorbyl glucoside, pyridoxine, skin-conditioning agents, humectants, occlusive agents, skin soothing agents, skin healing agents, panthenol, panthenol derivatives, ethyl panthenol, aloe vera, terpene alcohols, antioxidants, radical scavengers, pantothenic acid and its derivatives, allantoin, bisabolol, dipotassium glycyrrhizinate, skin treating agents, vitamin D compounds, mono-,di-, and tri-terpenoids, beta-ionol, cedrol, and their derivatives, glycerols, sorbitols, pentaerythritols, pyrrolidone acids and their salts, dihydroxyacetone, erythrulose, glyceraldehyde, tartaraldehyde, polysaccharides, essential fatty acids, salicylates, glycyrrhetinic acids, carotenoids, ceramides and pseudo-ceramides, lipid complexes, and combinations thereof.

9. The cosmetic or dermopharmaceutical composition of claim 1 wherein said compound is present in a solution, dispersion, emulsion, paste or powder, or is included individually or as a premix in vehicles constituted by carriers such as macro-, micro-, or nanocapsules, liposomes, oleosomes or chylomicrons, macro-, micro-, or nanoparticles or macro-, micro-, or nanosponges, macro-, micro-, or nanospheres, or adsorbed on organic polymer powders, talcs, bentonites, or other inorganic supports.

10. The cosmetic or dermopharmaceutical composition of claim 1 wherein said composition is in a form selected from the group consisting of a cream, lotion, ointment, gel, emulsion, dispersion, solution, suspension, cleanser, foundation, anhydrous preparation, sticks, lipstick, body oil, bath oil, shower gel, bath gel, emolient lotion, emollient milk, emollient cream, milk for care of skin or hair, cream for care of skin or hair, shampoo, scalp treatment lotion, sun-screen lotion, milk or cream, suntan lotion or cream, shaving cream or foam, aftershave lotion, mascara, nail varnish, skin "essences", serum, adhesive or absorbent material and transdermal patch.

11. A method of protecting and/or enhancing the state of the skin, preventing and/or treating imperfections of the skin of a person in need thereof comprising applying in a suitable amount and frequency a cosmetic or dermopharmaceutical composition comprising:
   a) at least one UGT inducer compound, said UGT inducer compound being present at a concentration from about 0.000001% (w/w) to about 10% (w/w);
   b) a chelating agent being N-hydroxysuccinimide present in an amount from about 0.00001% (w/w) to about 10% (w/w);
   c) at least one peptide, said peptide being present in an amount from about 0.000001% (w/w) to about 10% (w/w); and
   d) a cosmetically acceptable carrier to the skin of said person.

12. A method of treating rings under the eyes and/or hematoma in a person in need thereof comprising applying in a suitable amount and frequency a cosmetic or dermopharmaceutical composition comprising:
   a) at least one UGT inducer compound, said UGT inducer compound being present at concentration from about 0.000001% (w/w) to about 10% (w/w);
   b) a chelating agent being N-hydroxysuccinimide present in an amount from about 0.00001% (w/w) to about 10% (w/w);
   c) at least one peptide, said peptide being present in an amount from about 0.000001% (w/w) to about 10% (w/w); and
   d) a cosmetically acceptable carrier to the skin under the eyes and/or to the hematoma of said person.

13. The cosmetic or dermopharmaceutical composition of claim 4 wherein said plant extract is passion flower extract.

14. The cosmetic or dermopharmaceutical composition of claim 1 wherein said UGT inducer compound is present at concentration from about 0.0001% (w/w) to about 0.1% (w/w).

15. The cosmetic or dermopharmaceutical composition of claim 1 wherein said peptide includes at least one matrikine selected from the group consisting of N-Palmitoyl-Gly-His-Lys, N-Palmitoyl-Gly-Gln-Pro-Arg (SEQ ID NO:1), and a combination thereof.

16. The cosmetic or dermopharmaceutical composition of claim 3 wherein said analog of chrysin is selected from the group consisting of quercetin, apigenin, luteolin and diosmetin.

17. The cosmetic or dermopharmaceutical composition of claim 16 wherein said analog of chrysin is quercetin.

18. The method of claim 11 or 12 wherein said UGT inducer compound is chrysin, or an analog, stereoisomer, glycoside or derivative thereof.

19. The method of claim 18 wherein said analog of chrysin is selected from the group consisting of quercetin, apigenin, luteolin and diosmetin.

20. The method of claim 11 or 12 wherein said UGT inducer compound is chrysin.

21. The method of claim 11 or 12 wherein said peptide includes at least one matrikine selected from the group consisting of N-Palmitoyl-Gly-His-Lys, N-Palmitoyl-Gly-Gln-Pro-Arg (SEQ ID NO:1), and a combination thereof.

22. The composition of claim 1 wherein said UGT inducer compound is chrysin.

23. The composition of claim 22 wherein said peptide includes at least one matrikine selected from the group consisting of N-Palmitoyl-Gly-His-Lys, N-Palmitoyl-Gly-Gln-Pro-Arg (SEQ ID NO:1), and a combination thereof.

24. The method of claim 20 wherein said peptide includes at least one matrikine selected from the group consisting of N-Palmitoyl-Gly-His-Lys, N-Palmitoyl-Gly-Gln-Pro-Arg (SEQ ID NO:1), and a combination thereof.

25. The method of claim 11 or 12 wherein said UGT inducer compound is present at a concentration from about 0.00001% (w/w) to about 1% (w/w).

26. The method of claim 11 or 12 wherein said UGT inducer compound is present at a concentration from about 0.0001% (w/w) to about 0.1% (w/w).

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16)
      Sequence description: N-Palmitoyl-Gly-Gln-Pro-Arg

<400> SEQUENCE: 1

Gly Gln Pro Arg
1

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Lys Thr Thr Lys Ser
```

```
<210> SEQ ID NO 3
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16)
      Sequence description:
      N-Palmitoyl-Lys-Thr-Thr-Lys-Ser

<400> SEQUENCE: 3

Lys Thr Thr Lys Ser
1               5

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Arg Ser Arg Lys
1

<210> SEQ ID NO 5
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16)
      Sequence description:
      N-Palmitoyl-Tyr-Gly-Gly-Phe-Met

<400> SEQUENCE: 5

Tyr Gly Gly Phe Met
1               5

<210> SEQ ID NO 6
<211> LENGTH: 5
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: AMIDATION, Pal (C16)
      Sequence description:
      N-Palmitoyl-Tyr-Gly-Gly-Phe-Leu

<400> SEQUENCE: 6

Tyr Gly Gly Phe Leu
1               5

<210> SEQ ID NO 7
<211> LENGTH: 6
<212> TYPE: PRT
<213> ORGANISM: Artificial
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: AMIDATION, Pal (C16)
      Sequence description:
      N-Palmitoyl-Val-Gly-Val-Ala-Pro-Gly

<400> SEQUENCE: 7

Val Gly Val Ala Pro Gly
1               5

<210> SEQ ID NO 8
<211> LENGTH: 4
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acylation
      Sequence description:
      N-Acyl-Gly-Gln-Pro-Arg
<220> FEATURE:
<221> NAME/KEY: MOD_RES
<222> LOCATION: (1)..(1)
<223> OTHER INFORMATION: Acylation
      Sequence description:
      N-Acyl-Gly-Gln-Pro-Arg

<400> SEQUENCE: 8

Gly Gln Pro Arg
1
```